United States Patent
Wang et al.

(10) Patent No.: US 11,345,732 B2
(45) Date of Patent: May 31, 2022

(54) MODIFIED INTERLEUKIN 12 AND USE THEREOF IN PREPARING DRUGS FOR TREATING TUMOURS

(71) Applicants: BEIJING BIO-TARGETING THERAPEUTICS TECHNOLOGY INC., Beijing (CN); Zhengzhou University, Zhengzhou (CN)

(72) Inventors: Yaohe Wang, Henan (CN); Pengju Wang, Henan (CN); Lemoine Nick, Henan (CN); Dongling Gao, Henan (CN)

(73) Assignees: BEIJING BIO-TARGETING THERAPEUTICS TECHNOLOGY INC., Beijing (CN); Zhengzhou University, Zhengzhou (CN)

( * ) Notice: Subject to any disclaimer, the term of this patent is extended or adjusted under 35 U.S.C. 154(b) by 0 days.

(21) Appl. No.: 15/758,853

(22) PCT Filed: Sep. 9, 2016

(86) PCT No.: PCT/CN2016/098527
§ 371 (c)(1),
(2) Date: Mar. 9, 2018

(87) PCT Pub. No.: WO2017/041739
PCT Pub. Date: Mar. 16, 2017

(65) Prior Publication Data
US 2019/0010200 A1    Jan. 10, 2019

(30) Foreign Application Priority Data

Sep. 9, 2015    (CN) .......................... 201510568718.5

(51) Int. Cl.
*A61K 35/76* (2015.01)
*A61K 35/761* (2015.01)
*A61K 35/768* (2015.01)
*C07K 14/54* (2006.01)
*A61K 48/00* (2006.01)
*C12N 15/863* (2006.01)
*C12N 15/861* (2006.01)
*C12N 15/869* (2006.01)
*A61K 38/20* (2006.01)
*A61P 35/00* (2006.01)
*C12N 15/86* (2006.01)

(52) U.S. Cl.
CPC ........ *C07K 14/5434* (2013.01); *A61K 35/761* (2013.01); *A61K 38/20* (2013.01); *A61K 48/00* (2013.01); *A61P 35/00* (2018.01); *C07K 14/54* (2013.01); *C12N 15/86* (2013.01); *C12N 15/861* (2013.01); *C12N 15/863* (2013.01); *C12N 15/869* (2013.01); *C12N 2710/10043* (2013.01); *C12N 2710/10071* (2013.01); *C12N 2710/24143* (2013.01); *C12N 2710/24171* (2013.01)

(58) Field of Classification Search
None
See application file for complete search history.

(56) References Cited

U.S. PATENT DOCUMENTS

| | | | | |
|---|---|---|---|---|
| 2009/0142855 A1* | 6/2009 | Tang | ................... | C07K 14/5434 436/501 |
| 2013/0345295 A1* | 12/2013 | Wang | ................... | C07K 14/5434 514/44 R |
| 2017/0291934 A1* | 10/2017 | Reed | ................... | C07K 14/5434 |

FOREIGN PATENT DOCUMENTS

| | | |
|---|---|---|
| CN | 101410529 A | 4/2009 |
| JP | 2009500021 A | 1/2009 |
| JP | 2014509197 A | 4/2014 |

OTHER PUBLICATIONS

Picard et al., Inherited Interleukin-12 Deficiency: IL12B Genotype and Clinical Phenotype of 13 Patients from Six Kindreds. Am J. Hum. Genet., 2002, 70:336-348 (Year: 2002).*
Pan et al., Cancer Immunotherapy Using a Membrane-bound Interleukin-12 With B7-1 Transmembrane and Cytoplasmic Domains. Mol Therapy, 2012, 20:927-937 (Year: 2012).*
Ahmed et al., Selective expression of nonsecreted interferon by an adenoviral vector confers antiproliferative and antiviral properties and causes reduction of tumor growth in nude mice. J Interferon Cytokine Res . Jun. 2001;21(6):399-408 (Year: 2001).*
Giorgio Trinchieri, "Interleukin-12 and the regulation of innate resistance and adaptive immunity", Nature Reviews Immunology, vol. 3, No. 2, Feb. 1, 2003, pp. 133-146.
S Rose-John et al, "Intracellular retention of interleukin-6 abrogates signaling", Journal of Biological Chemistry, vol. 268, No. 29, Oct. 15, 1993, pp. 22084-22091.

(Continued)

*Primary Examiner* — Arthur S Leonard
(74) *Attorney, Agent, or Firm* — Fay Sharpe LLP

(57) ABSTRACT

The present invention discloses a modified interleukin 12 (nsIL-12) and its gene, recombinant vector and use in manufacture of a medicament for treatment of tumors. When the oncolytic adenovirus vector carrying the modified interleukin 12 gene targets tumor tissue, the modified interleukin 12 is continuously expressed at a low level and mainly distributed in the local tumor tissue, which improves the specificity to tumor cells and reduces the systemic toxicity of interleukin 12; the modified interleukin 12 shows stronger inhibitory effect on tumor growth in intraperitoneally disseminated tumors and orthotopic tumors, and has low toxicity. The modified interleukin 12 armed oncolytic viruses show excellent anti-tumor effects, with a significant regression of tumors and lower toxicity compared with the existing IL-12 armed virus.

5 Claims, 8 Drawing Sheets

Specification includes a Sequence Listing.

(56) References Cited

OTHER PUBLICATIONS

Extended European search report of counterpart EP application No. 16843677.2 dated Feb. 5, 2019.
Pan et al., "Enhancement of Canine Parvovirus VP2 DNA Vaccine Potency by Coadministration with Interleukin-12 Gene Expression Vector", Chinese Journal of Veterinary Science, vol. 32, No. 2, Feb. 29, 2012, pp. 196-201.
Xu et al., "Expression, Purification and Bioactivity Detection of Recombinant Human IL-12 in *Argyogramma agnate*", Virologica Sinica, vol. 17, No. 4, Nov. 30, 2002, pp. 340-343.
Wang et al., "Combined IL-12 and GM-CSF gene therapy for murine hepatocellular carcinoma", Cancer Gene Therapy, vol. 8, No. 10, Dec. 31, 2001, pp. 751-758.
Notice of Reasons for Refusal of Japanese application No. 2018-532498 dated Sep. 1, 2020.
Communication pursuant to Article 94(3) EPC of European application No. 16843677.2 dated Feb. 7, 2020.
Communication pursuant to Article 94(3) EPC of European application No. 16843677.2 dated Aug. 25, 2020.
Lieschke, G. J, et al., Bioactive murine and human interleukin-12 fusion proteins which retain antitumor activity in vivo, Nature Biotechnology, 1997, vol. 15(1), pp. 35-40.
Passer, B. J, et al., Combination of vinblastine and oncolytic herpes simplex virus vector expressing IL-12 therapy increases antitumor and antiangiogenic effects in prostate cancer models, Cancer Gene Therapy, 2013, vol. 20(1), pp. 17-24.
Pan, Wen-Yu et al., Cancer Immunotherapy Using a Membrane-bound Interleukin-12 With B7-1 Transmembrane and Cytoplasmic Domains, Molecular Therapy, 2012, vol. 20(5), pp. 927-937.
Jinghua Huang, et al., Therapeutic and Tumor-specific Immunity Induced by Combination of Dendritic Cells and Oncolytic Adenovirus Expressing IL-12 and 4-1BBL, 2010, vol. 18(2), pp. 264-274.
Zhi Yang, et al., Combined Therapy with Cytokine-Induced Killer Cells and Oncolytic Adenovirus Expressing IL-12 Induce Enhanced Antitumor Activity in Liver Tumor Model, 2012.
Reconsideration Report by Examiner before Appeal of counterpart Japanese application No. 2018-532498 dated Apr. 8, 2022.
Ho, M. et al., Isolation of anti-CD22 Fv with high affinity by Fv display on human cells; Proc. Natl. Acad. Sci. U S A., 2006, vol. 103 (25), pp. 9637-9642.
Zhang, J. et al., Mammalian cell display for rapid screening scFv antibody therapy; Acta Biochim. Biophys. Sin., vol. 46(10), 2014, pp. 859-866.
Davis, M. J. et al., Differential Use of Signal Peptides and Membrane Domains Is a Common Occurrence in the Protein Output of Transcriptional Units; PLoS Genet., 2006, vol. 2(4): e46 pp. 554-563.
Masao Sakaguchi, Topology formation of membrane proteins endoplasmic reticulum system and endoplasmic reticulum targeting evasion; 2003, No. 6, pp. 1-8, Seikagaku. The Journal of Japanese Biochemical Society.

* cited by examiner

MODIFIED INTERLEUKIN 12 AND USE THEREOF IN PREPARING DRUGS FOR TREATING TUMOURS

CROSS-REFERENCE TO RELATED APPLICATION

This application is a 371 of PCT Patent Application Serial No. PCT/CN2016/098527 filed Sep. 9, 2016, which claims the benefit of priority of the Chinese patent application filed on Sep. 9, 2015 by the Chinese Patent Office, Application No. 201510568718.5, entitled "Modified Interleukin 12 and Its Use in Preparation of a Medicament for Treatment of Tumors", which contents are incorporated herein by reference.

FIELD OF THE INVENTION

The present invention relates to the field of genetic engineering biotechnology and, in particular, to a modified interleukin 12 (hereinafter referred to as nsIL-12) and its gene, recombinant vector and use in the manufacture of medicament for the treatment of tumors.

BACKGROUND OF THE INVENTION

Interleukin 12 (IL-12) is an immunomodulatory cytokine secreted mainly by antigen-presenting cells such as dendritic cells, monocytes, macrophages and B cells, and is a heterodimer consisting of two subunits, p35 and p40, linking through a disulfide bond. The main function of IL-12 is involved in the differentiation of T cells, activating T cells and natural killer cells (NK cells), stimulating T cells and NK cells to secrete interferon γ, mediating NK cells and $CD^{8+}$ cytotoxic T cells, stimulating expression of IL-12 receptors, IL-12R-β1 and β2, involved in innate immunity and adaptive-immunity, and thus it is a multi-functional strong immune regulator.

At present, there are many laboratories studying the anti-tumor effect of IL-12 in a variety of ways, for example: transforming tumor cells by electroporation using IL-12-containing plasmids; transforming tumor cells by using IL-12 plasmid encapsulated in biodegradable microspheres; performing cancer therapy by using recombinant IL-12 protein, chimera of antibody and IL-12, immune cells expressing IL-12, adenovirus/retroviral vector containing IL-12, etc.; and conducting tumor therapy by using IL-12 in combination with chemotherapy, radiotherapy and immunotherapy. These studies have shown that these IL-12 can cause the regression and decrease of human and mouse tumor cells burden, as well as the reduction of angiogenesis in tumors. However, the in vivo half-lives of the various IL-12 as described above are very short, the sustained administration and relatively large doses (1 to 10 μg/day) for these IL-12s are usually required to achieve therapeutic effects, whereas high doses of IL-12 often leads to severe systemic side effects. Therefore, there is an urgent need to address the problems of short half-life and toxic side effects of IL-12 in vivo.

Systemic administration of IL-12 may cause potentially lethal toxicity, which prevents its clinical use so far. In order to clinically apply IL-12, many strategies for reducing the toxicity of IL-12 have been investigated and are still research hotspots now, and a series of methods for modifying IL-12 have been developed. For example, a system that relies on oral ligand drugs to control IL-12 expression can significantly reduce toxicity induced by IL-12, but it cannot effectively transduce tumor cells and is lack of simultaneously induced inflammatory responses, which limit the anti-tumor application of this method.

SUMMARY OF THE INVENTION

In order to apply the anti-tumor potency of IL-12, the present invention discloses a novel reconstructed IL-12 which has retained or enhanced anti-tumor ability, but its toxicity is dramatically decreased or eliminated. In the context, a modified IL-12 with deletion of N-terminal signal peptide is inserted into a novel tumor-targeted oncolytic virus vector to construct an oncolytic virus capable of expressing non-secretory IL-12, and its therapeutic effect and IL-12 function are disclosed as well. Based on this, the present invention provides a modified interleukin 12 (called nsIL-12) and its gene, recombinant vector and use in manufacture of a medicament for treatment of tumors.

In the first aspect of the present invention, there is provided a nucleotide sequence encoding a modified interleukin 12, which consists of the nucleotide sequence shown by SEQ NO: 1.

The nucleotide sequence encoding the modified interleukin 12 may also be a nucleotide sequence derived from a human interleukin 12 nucleotide sequence but different from the nucleotide sequence of SEQ ID NO: 1, and a protein encoded thereby exhibits an anti-tumor effect or may cause tumor regression and has lower toxic and side effects compared to the existing IL-12s.

In another aspect of the invention, there is provided a modified interleukin 12 encoded by the nucleotide sequence as described above.

Preferably, the modified interleukin 12 consists of the amino acid sequence shown by SEQ ID NO: 2.

The modified interleukin 12 may also consist of an amino acid sequence derived from human IL-12 but different from the amino acid sequence of SEQ NO: 2, and exhibits an anti-tumor effect or may cause tumor regression and has lower toxic and side effects as compared to the existing IL-12.

In another aspect of the invention, there is provided a recombinant vector comprising the nucleotide sequence encoding the modified IL-12.

Preferably, the recombinant vector is capable of targeting a tumor cell. More preferably, the recombinant vector can be obtained by construction of a vector selected from the group consisting of adenovirus vectors, vaccinia virus vectors, herpes simplex virus vectors.

In a preferred embodiment, the recombinant vector is oncolytic adenovirus vector Ad-TD-nsIL-12 (China Center for Type Culture Collection, Wuhan, China, Wuhan University, Accession No. CCTCC NO: V201520, date of deposit: May 21, 2015, human adenovirus serotype 5 mutant, also known as Ad-TD-nsIL12), which is an adenovirus serotype 5 of subclass C, but has deletion of three genes, E1A-CR2, E1B19K and E3gp19K, and E3gp19K promoter is used to control the expression of the modified IL-12 gene.

In another aspect of the invention, there is provided a use of the modified IL-12 or the nucleic acid sequence encoding the modified IL-12 or the vector in the manufacture of a medicament for the treatment of tumors.

Preferably, the tumors are solid tumor, an intraperitoneally disseminated tumor or a metastatic tumor.

The nucleotide sequence encoding the modified interleukin 12 is obtained by linking a gene encoding a modified human IL-12 p35 subunit (ns-p35, which nucleotide sequence is shown in SEQ NO: 3) to a gene encoding a modified human IL-12 p40 subunit (ns-p40, which nucleotide sequence is shown in SEQ NO: 4) via a short sequence (GTTCCTGGAGTAGGGGTACCTGGGG TGGGC).

The oncolytic adenovirus vector Ad-TD-nsIL-12 is an adenovirus serotype 5 (Ad5) of subclass C, but has deletion of three genes, E1A-CR2, E1B19K and E3gp19K, and E3gp19K promoter is used to control the expression of the modified IL-12 gene. The recombinant adenovirus vector can be selectively replicated in tumor cells and express the modified human IL-12 after entry into the tumors, in which the expression of the modified IL-12 is confined in the tumor cells; with the lysis of tumor cells, the expressed IL-12 is released, and tumor-associated antigens are released simultaneously, the released tumor-associated antigens and IL-12 show synergistic effect of inducing an efficient and specific anti-tumor response in vivo to further kill distant tumor cells including metastatic small tumor lesions that are not infected by viruses. These tumors include solid tumors, metastatic tumors and disseminated tumors that can be observed by naked eye or visible under microscope. The recombinant adenovirus vector has a stronger tumor growth inhibitory effect on an intraperitoneally disseminated tumor and an orthotopic tumor, and has a lower toxicity.

The method of constructing the oncolytic adenovirus vector Ad-TD-nsIL-12 for targeting therapy of human tumor comprises the following steps:

(1) Cloning nsIL-12 fusion gene: the total RNA of a cultured to RPMI-8866 cell is extracted and reverse transcribed into cDNA, a PCR is performed to clone a modified p35 subunit gene (ns-p35, which nucleotide sequence is shown in SEQ NO:3) and a modified p40 subunit gene (primer: p40-F: CCTACGTAATGATATGGGAACT-GAAGAAAG, p40-R: GCCCACCCCAGGTACCCC-TACTCCAGGAACACTGCAGGGCACA GATGC, ns-p40, which nucleotide sequence is shown in SEQ NO: 4) by using a primer (p35-F: GTTCCTG-GAGTAGGGGTACCTGGGGTGGGCGCCAG AAACCTCCCCGTG, p35-R: GCTACGTATTAG-GAAGCATTCAGATA) containing a SnaBI cleavage site and an elastin sequence (GTTCCTG-GAGTAGGGGTACCTGGGGTGGGC), the ns-p40 subunit gene fragment and the ns-p35 subunit gene fragment are ligated by PCR to form nsIL-12 complete gene fragment, and the nsIL-12 complete gene fragment is ligated into a cloning vector T vector, which is designated as T-nsIL-12; the T-nsIL-12 plasmid is digested with SnaBI to obtain nsIL-12 gene fragment (SEQ NO: 1);

(2) Construction of pSSE3gp19K shuttle vector: the multiple cloning sites at CHL upstream of pSS-CHL (see: FIG. 1) are digested with Sal1 and EcoRV, an upstream 1091 bp sequence of E3 6.7K gene termination codon is cloned by using a primer containing Sal1 and EcoRV cleavage sites at two ends thereof, which is used as left arm and ligated to pSS-CHL to form pSSE3gp19K-L; the pSSE3gp19K-L is digested with SnaB1 and Xho1, and a downstream 1146 bp sequence of E3gp19K gene termination codon is cloned by using a primer containing SnaB1 and Xho1 cleavage sites at two ends thereof, and both of them are ligated to from pSSE3gp19K shuttle vector;

(3) Construction of pSSE3gp19K-nsIL-12 vector: the pSSE3gp19K vector is digested with EcoRV and its terminal phosphate group is removed with phosphatase, then it is ligated with the nsIL-12 gene fragment to produce the pSSE3gp19K-nsIL-12 vector, which sequence is determined by sequencing analysis;

(4) Construction of Ad-TD-nsIL-12-CHL: the pSSE3gp19K-nsIL-12 is linearized with Pme1, a large fragment containing nsIL-12 is recovered, homologous recombination with pAd-TD vector (see patent: ZL200910066130.4) is performed via electroporation in BJ5183 competent cells, and positive clone pAd-TD-nsIL-12-CHL is picked up;

(5) Construction of pAd-TD-nsIL-12: the positive vector pAd-TD-nsIL-12-CHL is digested with Swa1 to delete CHL gene, after inactivation of Swa1 and T4 ligase, it is used to transform TOP10 competent cells to obtain pAd-TD-nsIL-12 vector; and (6) Construction of Ad-TD-nsIL-12 virus vector: the recombinant pAd-TD-nsIL-12 vector is linearized with Pad and transfected into 293 cells to produce the recombinant adenovirus vector Ad-TD-nsIL-12.

The present invention provides a modified IL-12 which is non-secretory. Since the modified IL-12 provided by the present invention lacks N-terminal signal peptide, it cannot be secreted out of the cells when it is expressed. The modified IL-12 of the present invention includes any natural IL-12 and variants thereof, for example, those obtained by means of genetic engineering or protein engineering, provided that such modified IL-12 is a non-secretory IL-12 that does not contain a signal peptide but retains anti-tumor activity. Based on the present disclosure, those skilled in the art can obtain a variety of modified IL-12s as described in the present invention and verify their activities (see, for example, Gene Therapy. 2015 September; 22 (9): 696-706).

Accordingly, the present invention specifically provides a modified IL-12, which is non-secretory.

Preferably, the modified IL-12 of the present invention has the following structure:

p40-linker-p35 or p35-linker-p40;

wherein the non-secretory IL-12 does not contain a secretory signal peptide. Preferably, neither p40 nor p35 in the above structure contains a signal peptide.

For "linker", a person skilled in the art can design or select a suitable linker derived from a variety of known linkers according to the prior art (e.g., Adv Drug Deliv Rev. 2013 Oct. 15; 65 (10): 1357-1369; and Front Immunol. 2015 Apr. 7; 6: 136). Preferably, the linker has a sequence of (GTTCCTGGAGTAGGGGTACCTGGGGTGGGC). It will be understood by those skilled in the art that based on the present disclosure, those skilled in the art can design linkers with various other sequences (J Biomed Nanotechnol. 2015 August; 11 (8): 1418-30).

Of course, it is also possible to separately express a signal peptide-free p35 and a signal peptide-free p40 via oncolytic virus, and to bind p35 and p40 intracellularly (e.g., via disulfide bonds) and produce an IL-12 without secretory signal peptide.

The p35 and p40 include any natural p35 and p40 as well as variants thereof, such as variants obtained by means of genetic engineering or protein engineering, provided that the variants retain the activity of natural p35 and p40. Preferably, p35 and p40 are natural human p35 and human p40, as well as variants thereof. More preferably, the p35 has or consists of the sequence of SEQ NO: 5; and p40 has or consists of the sequence of SEQ NO: 6.

Variants of the invention may comprise or consist of an amino acid sequence which is obtained by substitution, deletion, insertion or addition of one or several amino acids on the basis of its natural amino acid sequence or parental sequence and retains the activity before the substitution, deletion, insertion or addition.

By way of example, p35 may comprise or consist of an amino acid sequence which is obtained by substitution, deletion, insertion or addition of one or several amino acids on the basis of its natural amino acid sequence or parental sequence and retains the activity before the substitution, deletion, insertion or addition. For example, p35 may comprise or consist of an amino acid sequence which is obtained by substitution, deletion, insertion or addition of one or several amino acids on the basis of SEQ NO: 5 and retains the activity before the substitution, deletion, insertion or addition.

By way of example, p40 may comprise or consist of an amino acid sequence which is obtained by substitution, deletion, insertion or addition of one or several amino acids on the basis of its natural amino acid sequence or parental sequence and retains the activity before the substitution, deletion, insertion or addition. For example, p40 may comprise or consist of an amino acid sequence which is obtained by substitution, deletion, insertion or addition of one or several amino acids on the basis of SEQ NO: 6 and retains the activity before the substitution, deletion, insertion or addition.

In the present invention, the substitution, deletion, insertion or addition of one or several amino acids in an amino acid sequence refers to substitution, deletion, insertion or addition of one or several amino acids (for example, 2, 3, 4, 5, 6, 7, 8 or 9 amino acids) at any one or several sites in the amino acid sequence, and any two or more of the substitutions, deletions, insertions or additions may occur at the same time.

The method of the present invention for substitution, deletion, insertion or addition of one or several amino acids in an amino acid sequence can be carried out by site directed mutagenesis method as disclosed in "Molecular Cloning 3" and "Current Protocols in Molecular Biology" and the like.

For the substitution described in the present invention, the substitution of amino acid residues is preferably carried out within each of the following groups:
  1: leucine, valine, alanine, methionine, serine, glycine
  2: aspartic acid, glutamic acid;
  3: asparagine, glutamine;
  4: lysine, arginine;
  5: proline, hydroxyproline;
  6: serine, threonine; and
  7: phenylalanine, tyrosine.

For the activity before the conservative substitution, deletion, insertion or addition described herein, the activity of the protein or amino acid sequence after substitution, deletion, insertion or addition is more than 10%, more than 20%, more than 40%, more than 60%, more than 80%, more than 90%, more than 95%, more than 96%, more than 97%, more than 98%, more than 99%, or 100% or more of the activity before the substitution, deletion, insertion or addition.

The number of amino acid residues for the substitution, deletion, insertion and/or addition as described above is generally preferably a small number. The variant is an amino acid sequence having an identity of about 60% or more, about 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more to its parent or natural amino acid sequence, and having the activity of its parent or natural amino acid sequence. In general, the above-mentioned identity preferably has a large value.

The variant of the present invention also include an amino acid sequence having an identity of at least about 60% or more, about 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more to its natural amino acid sequence or parental sequence, and having the activity of its natural amino acid sequence or parental sequence. In general, the above-mentioned identity preferably has a large value.

By way of example, p35 also includes an amino acid sequence having an identity of at least about 60% or more, about 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more to its natural amino acid sequence or parental sequence (e.g., SEQ NO:5), and having the activity of its natural amino acid sequence or parental sequence. In general, the above-mentioned identity preferably has a large value.

By way of example, p40 also includes an amino acid sequence having an identity of at least about 60% or more, about 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more to its natural amino acid sequence or parental sequence (e.g., SEQ NO:6), and having the activity of its natural amino acid sequence or parental sequence. In general, the above-mentioned identity preferably has a large value.

Preferably, the present invention specifically provides a modified IL-12 which is non-secretory and has or consists of the amino acid sequence shown by SEQ ID NO: 2.

By way of example, the modified non-secretory IL-12 of the present invention may comprise or consist of an amino acid sequence having substitution, deletion, insertion or addition of one or several amino acids on the basis of SEQ NO: 2 and retaining the activity of SEQ NO: 2.

By way of example, the modified non-secretory IL-12 of the present invention may include an amino acid sequence having an identity of at least about 60% or more, about 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more to SEQ NO:2, and having the activity of SEQ NO:2. In general, the above-mentioned identity preferably has a large value.

In the present invention, "non-secretory" means that the gene encoding a target protein is lack of a fragment encoding a signal peptide, so that the synthesized protein cannot be transported to a secretion-related endoplasmic reticulum-Golgi-plasma membrane system, and thus cannot be secreted extracellularly.

The present invention also provides a nucleotide sequence encoding the modified non-secretory IL-12 according to the present invention. Preferably, it comprises or consists of the nucleotide sequence shown by SEQ ID NO: 1 or a complementary sequence thereof.

Preferably, the nucleotide sequence encoding the modified non-secretory IL-12 according to the present invention comprises or consists of the following sequence:
a) the nucleotide sequence shown in SEQ NO: 1;
b) a polynucleotide capable of hybridizing under stringent conditions to the nucleotide sequence of SEQ NO: 1 and encoding an amino acid sequence having non-secretory IL-12 activity; or
c) a complementary sequence of the above a) or b).

In the text, having non-secretory IL-12 activity means that a certain protein or amino acid sequence has an activity of 10% or more, 20% or more, 40% or more and 60% or more, 80% or more, 90% or more, 95% or more, 96% or more, 97% or more, 98% or more, 99% or more, or 100% or more of that of the non-secretory IL-12 (SEQ NO. 2).

It is further preferred that the nucleotide sequence encoding the modified non-secretory IL-12 according to the present invention comprises or consists of the following sequence:
a) the nucleotide sequence shown in SEQ NO: 1;
b) a polynucleotide capable of hybridizing under stringent conditions to the nucleotide sequence of SEQ NO: 1 and encoding an amino acid sequence having non-secretory IL-12 activity; or
c) a complementary sequence of the above a) or b).

The "stringent conditions" described herein may be either lowly stringent conditions, moderately stringent conditions, or highly stringent conditions, preferably highly stringent conditions. Illustratively, "lowly stringent conditions" may be conditions of 30° C., 5×SSC, 5×Denhardt solution, 0.5% SDS, 52% formamide; "moderately stringent conditions" may be conditions of 40° C., 5×SSC, Denhardt solution, 0.5% SDS, 52% formamide; "highly stringent conditions" may be conditions of 50° C., 5×SSC, 5×Denhardt liquid, 0.5% SDS, 52% formamide. Those skilled in the art will appreciate that the higher the temperature, the higher the identity of the obtained polynucleotide. In addition, one skilled in the art can select a combination of factors such as temperature, probe concentration, probe length, ionic strength, time, salt concentration, and the like that affect the stringency of hybridization to achieve the corresponding stringency.

In addition, when identity calculation is performed with a homology searching software such as FASTA, BLAST and the like using default parameters, the hybridizable polynucleotide can be a polynucleotide having an identity of about 60% or more, about 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 99% or more, 99% or more, 99.1% or more, 99.2 or more, 99.3% or more, 99.4% or more, 99.5% or more, 99.6% or more, 99.7% or more, 99.8% or more, or 99.9% or more to the polynucleotide sequence encoding the modified non-secretory IL-12 of the present invention.

The identity of amino acid sequences or nucleotide sequences can be determined with the algorithm BLAST of Karlin and Altschul (Proc. Natl. Acad. Sci. USA 87: 2264-2268, 1990; Proc. Natl. Acad. ScL USA 90: 5873, 1993). Programs BLASTN and BLASTX based on BLAST algorithm have been developed (Altschul S F, et al: J Mol Biol 215: 403, 1990). When using BLASTN to analyze amino acid sequence, the parameters may be: score=100, wordlength=12; in addition, when using BLASTX to analyze amino acid sequence, the parameters may be: score=50, wordlength=3; when using BLAST and Gapped BLAST, the parameters for each of programs can be their default parameter values.

The present invention also provides a recombinant vector, such as a plasmid vector or a viral vector, comprising the nucleotide sequence of the present invention or being capable of expressing the modified non-secretory IL-12 of the present invention. In addition, the present invention also provides a microorganism (e.g., a bacterium) or a cell, for example, *Escherichia coli* and yeast, to which the recombinant vector of the present invention or the nucleotide sequence of the present invention is introduced. The cell into which the recombinant vector of the present invention is introduced is preferably a cell derived from human cells, such as cells derived from human tissues or organs, such as a cell or stem cell derived from human liver, kidney, pancreas, stomach, large intestine, small intestine, more preferably a cancer cell or a stem cell.

Preferably, the recombinant vector comprising the nucleotide sequence of the invention is an adenovirus serotype 5 vector, a vaccinia virus vector, an adenovirus serotype 11 vector, a herpes virus, a reovirus, a measles virus, a Newcastle disease virus, a vesicular stomatitis virus, a poliovirus and so on.

More preferably, the vector comprising the nucleotide sequence of the present invention is an oncolytic adenovirus vector Ad-TD-nsIL-12 (China Center for Type Culture Collection, Wuhan, China, Wuhan University, Accession No. CCTCC NO: V201520, date of deposit: May 21, 2015, human adenovirus serotype 5 mutant).

The present invention also provides a kit or a medicament, which comprises the modified non-secretory IL-12 of the present invention, a nucleotide sequence encoding the modified non-secretory IL-12 of the present invention, a vector capable of expressing the modified non-secretory IL-12 of the present invention, or a vector comprising the nucleotide sequence of the present invention. Preferably, the kit or medicament is used for the treatment or prevention of a disease associated with IL-12.

The present invention also provides a use of the modified non-secretory IL-12 of the present invention, a nucleotide sequence encoding the modified non-secretory IL-12 of the present invention, a vector capable of expressing the modified non-secretory IL-12 of the present invention, or a vector comprising the nucleotide sequence of the present invention in manufacture of a kit or a medicament for the treatment of a disease (e.g., cancer) associated with IL-12 in a subject.

The present invention also provides a method for treating a disease (e.g., cancer) associated with IL-12 in a subject, comprising administering to the subject an effective amount of the modified non-secretory IL-12 of the present invention, a nucleotide sequence encoding the modified non-secretory IL-12 of the present invention, a vector capable of expressing the modified non-secretory IL-12 of the present invention, or a vector comprising the nucleotide sequence of the present invention Preferably, the subject is a mammal, more preferably a human.

As used in the text, "disease associated with IL-12" preferably refers to a disease, such as cancer, that can be treated or prevented by the use of IL-12.

Although the present invention exemplifies pancreatic cancer, head and neck cancer, lung cancer, esophageal cancer, ovarian cancer, colorectal cancer, colon cancer and gastric cancer, the term "cancer" may be a solid tumor, an intraperitoneally disseminated tumor or a metastatic tumor, including, but not limited to, primary melanoma, metastatic melanoma, adenocarcinoma, squamous cell carcinoma, squamous gland cell carcinoma, thymoma, sarcoma, non-Hodgkin's lymphoma, Hodgkin's lymphoma, leukemia, prostate cancer, ovarian cancer, pancreatic cancer, colon cancer, multiple myeloma, neuroblastoma, NPC (nasopharyngeal carcinoma), bladder cancer, cervical cancer, kidney cancer, brain cancer, bone cancer, stomach cancer, esophageal cancer, colorectal cancer (e.g., rectal cancer and duodenal cancer), liver cancer, lung cancer, bone cancer, bladder cancer, ovarian cancer, lymphoma, blood cancer, breast cancer, head and neck cancer, uterine cancer, melanoma and other cancers, as well as cancer symptoms. Preferably, the cancer treated with the present invention is preferably, the pancreatic cancer, kidney cancer, head and neck cancer, lung cancer, esophageal cancer, breast cancer, ovarian cancer, colorectal cancer or gastric cancer and relevant symptoms thereof.

The modified non-secretory IL-12 of the present invention, a nucleotide sequence encoding the modified non-secretory IL-12 of the present invention, a vector capable of expressing the modified non-secretory IL-12 of the present invention, or a vector comprising the nucleotide sequence of the present invention, which acts as active ingredient, may be used together with a pharmaceutically acceptable carrier. In addition to the active ingredient, the methods, uses and products of the present invention may further comprise a suitable pharmaceutically acceptable carrier, including an excipient and an adjuvant that facilitate the processing of the active ingredient into a preparation.

For example, a preparation suitable for injection or infusion includes aqueous and non-aqueous sterile injectable solutions and aqueous and non-aqueous sterile suspensions, in which the sterile injectable solutions may optionally comprise an antioxidant, a buffer, a bacteriostat and a solute capable of equilibrating pressure between the preparation and the blood of a subject, and the sterile suspension may comprise a suspending agent and a thickening agent. The preparation may be present in a unit dose or multi-dose container, such as a sealed ampoule, and may be stored under freeze-drying (lyophilizating) conditions, requiring only the addition of a sterile liquid carrier such as water for injection before immediate uses.

The active ingredient of the present invention may optionally be combined with a solid excipient, and optionally the resulting mixture is ground and, if desired, after the addition of a suitable adjuvant, the mixture of particles is processed to obtain the desired dosage form. The suitable excipient is especially a filler such as a sugar, including lactose, sucrose, mannitol or sorbitol; cellulose or starch preparations, gelatin, tragacanth, methylcellulose, hydroxypropylmethylcellulose, carboxylmethylcellulose sodium and/or polyvinylpyrrolidone (PVP). If desired, a disintegrating agent such as a crosslinked polyvinylpyrrolidone, agar or alginic acid or a salt thereof such as sodium alginate may be added.

An effective amount of the active ingredient of the present invention may be any dosage capable of treating cancer, or relieving cancer symptoms or inhibiting cancer cells, which may be a dosage unit corresponding to about 0.1-15 mg of the active ingredient, preferably 0.2-12 mg of the active ingredient. More preferably, the dosage unit comprises about 2 to 5 mg of the active ingredient. Most preferably, the dosage unit comprises about 3-4 mg of the active ingredient. The determination of effective amount is within the capabilities of those skilled in the art, particularly in light of the disclosure provided herein.

According to the present invention, the pharmaceutical product (medicament or kit) of the present invention may be administered to a subject in any effective amount of dose. Preferably, the pharmaceutical product (medicament or kit) of the present invention may be administered in multiple doses, for example, from about 2 to about 15 doses, more preferably from about 4 to 10 doses, and most preferably about 6 doses. In a particularly preferred embodiment, the pharmaceutical product (medicament or kit) of the present invention is administered to a subject via, for example injection, infusion or oral administration, at a frequency of about once every other day during the administration. In a particularly preferred embodiment, the administration is carried out by injection or infusion, most preferably by intratumoral injection.

It is to be understood that the pharmaceutical product (medicament or kit) of the present invention may be formulated in any suitable manner for administration via any suitable route.

The dosage unit of the pharmaceutical product (medicament or kit) of the present invention is based on a conventional administration of a subject. For example, the dosage unit can be administered more than once a day, once every two days, once a week, once a month, etc. The dosage unit can be administered on a twice/week basis, i.e., twice a week, for example once every three days.

The present invention also provides a method for preparing the recombinant vector of the present invention, comprising inserting a nucleotide sequence encoding the modified non-secretory IL-12 of the present invention into a vector to obtain a recombinant vector capable of expressing the non-secretory IL-12; and performing transfection of the recombinant vector into a cell to produce the recombinant virus of the invention.

As used in the text, "comprising" is synonymous with "including", "containing" or "being characterized in", is inclusive or open, and does not exclude additional elements or method steps that are not stated. When the term "comprising" is used in any expression herein, particularly in describing the method, use or product of the present invention, it should be understood the method, use or product encompasses those products, methods and uses substantially consisting of or by the components or elements or steps and those products, methods and uses consisting of or by the components or elements or steps. The exemplarily described embodiments of the present invention may be carried out in the absence of any one or more of elements, one or more of the limitations, that are not specifically disclosed herein.

In the pharmaceutical product of the present invention, an instruction relating to the pharmaceutical product may contain the following contents: indications (cancer, e.g., pancreatic cancer), dosage of administration (e.g., those exemplarily illustrated above), and possible side effects.

The recombinant vector of the present invention (e.g., recombinant oncolytic virus) can be selectively replicated in tumor cells or cancer cells and express the modified non-secretory IL-12 after entering the tumor or cancer cells, the expression of the modified non-secretory IL-12 is confined in the tumor cells or cancer cells due to the lack of signal peptide sequence; with the lysis of tumor cells or cancer cells, the expressed IL-12 is released, and tumor-associated antigens or cancer-related antigens is released simultaneously, thus the released tumor-associated antigens or cancer cell-associated antigens acts synergistically with IL-12 to produce an efficient, specific anti-tumor or anti-cancer response in body to further kill distant tumor cells or cancer cells including micrometastases or cancerous lesions that are not infected by viruses. These tumors or cancers include solid tumors, metastatic tumors and diffused tumors that can be seen under naked eyes or visible under a microscope. The inventors of the present invention have surprisingly found that the recombinant vector (for example, recombinant oncolytic virus) comprising a nucleotide sequence encoding IL-12 without a signal peptide is capable of expressing IL-12 protein at a stable, sustained and low level, thereby overcoming the drawbacks of the existing IL-12 protein such as short half-life and toxic and side effects caused by high level of expression; in addition, it has a stronger tumor growth inhibitory effect and has no significant toxicity. Moreover, the recombinant vector (for example, recombinant oncolytic virus) comprising a nucleotide sequence encoding IL-12 without a signal peptide has a stronger tumor growth inhibitory effect on tumors or cancers (e.g., intraperitoneally disseminated tumors and in situ tumors) and low toxicity.

In contrast, if the IL-12 expressed in the recombinant vector (e.g., oncolytic virus) contains a signal peptide, the expressed IL-12 with the signal peptide would be secreted out of tumor cells or cancer cells in time so that the body suffers from a challenge of IL-12 with a larger dose, and thus greater toxic and side effects on the body would occur. In addition, since the IL-12 expressed by the recombinant vector is prematurely secreted out of tumor cells or cancer cells, the body would not be able to effectively recruit an effective amount of IL-12 to act synergistically with the released tumor-associated antigens or cancer cell-associated antigens when the recombinant vector (e.g., oncolytic virus) lyses the tumor cells or cancer cells and releases the tumor-associated antigens or cancer cell-associated antigens. Thus, in comparison with the recombinant vector (e.g., recombinant oncolytic viruses) comprising a nucleotide sequence encoding IL-12 without signal peptide, the recombinant vector (e.g., recombinant oncolytic viruses) comprising a nucleotide sequence encoding IL-12 with signal peptides has stronger toxic and side effects, and cannot make the body produce an efficient, specific anti-tumor or anti-cancer response.

The terms and expressions recited in the text are used as descriptive rather than restrictive terms, and any equivalents of the features and portions thereof as described herein are not intended to be excluded from, and it should be appreciated that various modifications are possible within the scope of the invention. It is therefore to be understood that while the invention has been specifically disclosed by way of preferred embodiments and optional features, those skilled in the art may employ modifications and variations of the concepts disclosed herein and such modifications and variations are considered to be within the scope of the present invention as defined in the appended claims.

The present invention will now be described in more detail with reference to the following examples, but these examples are merely illustrative of the present invention and are not to be construed as limiting the present application.

The beneficial effects of the present invention are:

1. Compared with existing IL-12s, the modified IL-12 of the present invention is mainly distributed in local tumor tissue, which enhances the specificity to tumor cells and reduces the systemic side effects of IL-12;

2. The method of the present invention utilizes a tumor-targeted viral vector to express the modified IL-12, which can make IL-12 protein to be expressed at a stable, sustained and low level, overcome the shortfalls of the existing IL-12 protein, such as short half-life, and toxic and side effects caused by high level expression;

3. Compared with existing IL-12s, the modified IL-12 of the present invention has a stronger tumor growth inhibitory effect on intraperitoneally disseminated tumors and in situ tumors and has no significant toxicity.

The oncolytic adenovirus Ad-TD-nsIL-12 of the present invention can be used not only for intratumoral injection but also for intraperitoneal and intra-thoracic injection, which reduces the difficulty of administration and expands the range of treatable patients, in which all of patients with tumors at different sites can get good therapeutic effects and will not suffer from significant side effects.

DEPOSIT OF BIOLOGICAL MATERIAL

Figure 1:
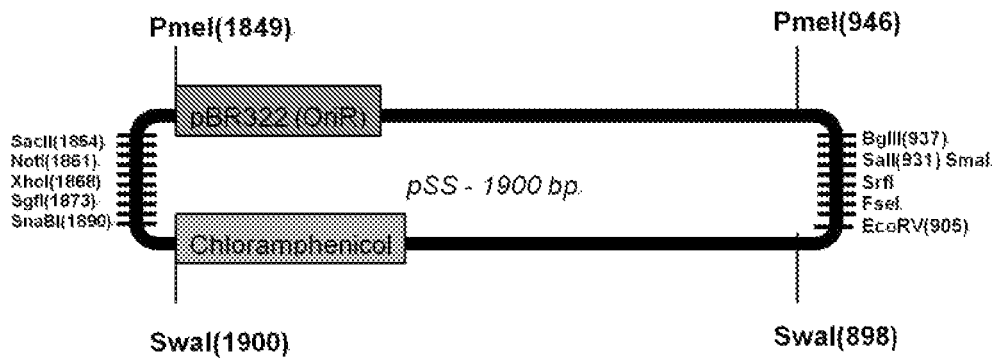
FIG. 1: pSS-CHL plasmid map.

The following biological material has been deposited with the China Center For Type Culture Collection (ATCC), Wuhan University, Wuhan 430072 P. R. China

| Vector Designation | CCTCC No. | Deposit Date |
|---|---|---|
| Ad-TD-nsIL-12 | V201520 | May 21, 2015 |

This deposit was made under the provisions of the Budapest Treaty on the International Recognition of the Deposit of Microorganisms for the Purpose of Patent Procedure. This assures the maintenance of a viable culture of the deposit for 30 years from the date of deposit and for at least five (5) years after the most recent request for furnishing of a sample of the deposit. The deposit will be made available by the CCTCC under the terms of the Budapest Treaty, and subject to an agreement between the depositor and the CCTCC, which assures that all restrictions imposed by the depositor on the availability to the public of the deposited material will be irrevocably removed upon the granting of the pertinent U.S. patent, assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. § 122 and the Commissioner's rules pursuant thereto (including 37 C.F.R. § 1.14 with particular reference to 886 OG 638).

DETAILED DESCRIPTION OF THE INVENTION

The present invention is further illustrated by way of examples, which are not intended to limit the scope of the invention, and those skilled in the art will be able to make modifications to these embodiments in light of the teachings of the present invention without departing from the spirit and scope of the invention to obtain similar or same results, and all of these modifications are within the scope of the present invention.

EXAMPLE 1

Method for Construction of Oncolytic Adenovirus Serotype 5 Vector Ad-TD-nsIL-12 for Targeting Therapy of Human Tumors, Comprising the Steps of (1) Cloning nsIL-12 fusion gene: the total RNA of cultured RPMI-8866 cell was extracted and reverse transcribed into cDNA, a PCR assay was performed to clone a modified p35 subunit gene (ns-p35, which nucleotide sequence was shown in SEQ NO:3) and a modified p40 subunit gene (primer: p40-F: CCTACGTAATGATATGGGAACT-GAAGAAAG, p40-R: GCCCACCCCAGGTACCCC-TACTCCAGGAACACTGCAGGGCACA GATGC, ns-p40, which nucleotide sequence was shown in SEQ NO: 5) by using a primer (p35-F: GTTCCTG-GAGTAGGGGTACCTGGGGTGGGCGCCAG AAACCTCCCCGTG, p35-R: GCTACGTATTAG-GAAGCATTCAGATA) containing a SnaBI cleavage site and an elastin sequence (GTTCCTG-GAGTAGGGGTACCTGGGGTGGGC), the ns-p40 subunit gene fragment and the ns-p35 subunit gene fragment were ligated by PCR to form nsIL-12 complete gene fragment, and the nsIL-12 complete gene fragment was ligated into a cloning vector T vector, which was designated as T-nsIL-12; the T-nsIL-12 plasmid was digested with SnaBI to obtain nsIL-12 gene fragment for standby use (SEQ NO: 1);

(2) Construction of pSSE3gp19K shuttle vector: the multiple cloning sites at CHL upstream of pSS-CHL (see: FIG. 1) were digested with SaI1 and EcoRV, an upstream 1091 bp sequence of E3 6.7K gene termination codon was cloned by using a primer containing SaI1 and EcoRV cleavage sites at two ends thereof, used as left arm and ligated to pSS-CHL to form pSSE3gp19K-L; the pSSE3gp19K-L was digested with SnaB1 and Xho1, and a downstream 1146 bp sequence of E3gp19K gene termination codon was cloned by using a primer containing SnaB1 and Xho1 cleavage sites at two ends thereof, and both of them were ligated to form pSSE3gp19K shuttle vector;

(3) Construction of pSSE3gp19K-nsIL-12 vector: the pSSE3gp19K vector was digested with EcoRV and its terminal phosphate group was removed with phosphatase, then it was ligated with the nsIL-12 gene fragment to produce the p55E3gp19K-nsIL-12 vector, which sequence was determined by sequencing analysis;

(4) Construction of Ad-TD-nsIL-12-CHL: the pSSE3gp19K-nsIL-12 was linearized with Pme1, a large fragment containing nsIL-12 was recovered, homologous recombination with pAd-TD vector (see patent: ZL200910066130.4) was performed by electroporation in BJ5183 competent cells, and positive clones pAd-TD-nsIL-12-CHL were picked out;

(5) Construction of pAd-TD-nsIL-12: the positive vector pAd-TD-nsIL-12-CHL was digested with Swa1 to delete CHL gene, after inactivation of Swa1 and T4 ligase, it was used to transform TOP10 competent cells to obtain pAd-TD-nsIL-12 vector; and (6) Construction of Ad-TD-nsIL-12 virus vector: the recombinant pAd-TD-nsIL-12 vector was linearized with Pac1 and transfected into 293 cells to produce the recombinant adenovirus vector Ad-TD-nsIL-12.

3. The recombinant Ad-TD-nsIL-12 vector was linearized with Pac1 and transfected into 293 cells to produce the recombinant adenovirus vector Ad-TD-nsIL-12 (human adenovirus serotype 5 mutant, China Center for Type Culture Collection, Wuhan, China, Wuhan University, Accession No. CCTCC NO: V201520, date of deposit: May 21, 2015), also known as Ad-TD-nsIL12.

EXAMPLE 2

Method for Construction of Vector VV-TK-nsIL-12 of Oncolytic Vaccinia Virus for Target Therapy of Human Tumor, Comprising the Steps of 1. Construction of Shuttle Vector pVV-TK-nsIL-12

Figure 2:
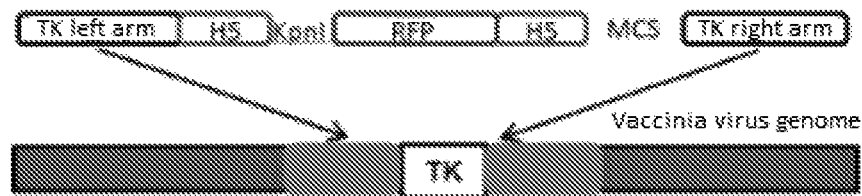
FIG. 2: pVV-TK plasmid map.
Figure 3:
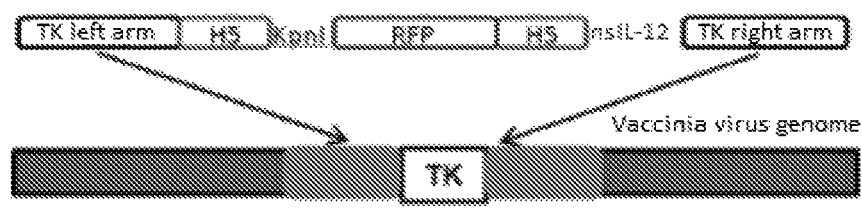
FIG. 3: pVV-TK-nsIL-12 plasmid map.

As described in Example 1, nsIL-12 gene was cloned with a primer containing Sal1 and Nhe1 cleavage sites, and digested with corresponding enzymes for standby application, pVV-TK plasmid was digested with Sal1 and Nhe1 (see FIG. 2, construction was performed by the method as published by the inventors, Mol Ther Methods Clin Dev. 2015 Sep. 16; 2:15035. doi: 10.1038/mtm. 2015.35. eCollection 2015), the nsIL-12 gene was ligated with pVV-TK to construct the pVV-TK-nsIL-12 vector (FIG. 3).

2. Recombination of VV-TK-nsIL-12 Viral Vector

Figure 4:
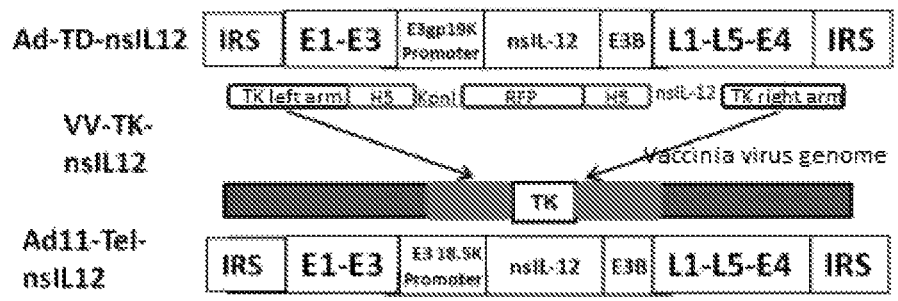
FIG. 4: Schematic diagrams of adenovirus serotype 5 vector Ad-TD-nsIL-12, Vaccinia virus vector VV-TK-nsIL-12 and type 11 adenovirus vector Ad11-Tel-nsIL-12.

CV1 cells were cultured, and then the CV1 was inoculated into a 96-well plate. When the cells grew to 90% confluence, they were transfected with CRISP-cas9 and gRNA plasmid, then infected with vaccinia virus VVL15 after 24 hours, and transfected with pVV-TK after 2 hours. After 24 hours, they were observed under a fluorescence microscope and the red fluorescent cell clones were picked out, which demonstrated that the VV-TK-nsIL-12 virus vector (FIG. 4) was successfully recombined.

3. Screening of VV-TK-nsIL-12 Virus Vector

The picked red fluorescent clones were frozen and thawed once, then infected CV1 cells again, the red fluorescent clones were picked, this screening process was repeated 5 times, and CV1 cells were infected to produce the virus. Its genome was extracted for sequencing.

EXAMPLE 3

Method for Construction of Vector Ad11-Tel-nsIL-12 of Oncolytic Adenovirus Serotype 11 for Target Therapy of Human Tumor, Comprising the Steps of 1. Construction of Shuttle Vector pSSE3-18.5K-nsIL-12 Containing nsIL-12

(1) Construction of pSSE3-18.5K: multiple cloning sites of pSS-CHL (constructed on the basis of pBR322 plasmid, see FIG. 1) were digested with SnaB1 and Xho1, E3 16.1K gene stop codon upstream 535 bp sequence was cloned by using a primer containing SnaB1 and Xho1 cleavage sites at two ends, used as the left arm and ligated to pSS-CHL, so as to form pSSE3-18.5K-L; the pSSE3-18.5K-L was digested with Sal1 and EcoRV, a downstream 584 bp sequence of E3-18.5K gene stop codon was cloned by using a primer containing Sal1 and EcoRV cleavage sites at two ends, and the two were ligated to form pSSE3-18.5K shuttle vector;

(2) Construction of pSSE3-18.5K-nsIL-12 vector: the pSSE3-18.5K vector was digested with SnaB1, and terminal phosphate group was removed by using phosphatase, then it was ligated to nsIL-12 gene fragment to produce pSSE3-18.5K-NsIL-12 vector, the sequencing analysis thereof was performed;

(3) The pSSE3gp19K-nsIL-12 was linearized with Pme1, large fragments containing nsIL-12 were recovered, homologous recombination with Ad11-Tel-GFP (see construction method in patent ZL201110143385.3) was performed via electroporation in BJ5183 competent cells, and positive clones Ad11-Tel-nsIL-12 (see FIG. 4) were picked out.

2. The recombinant Ad11-Tel-nsIL-12 vector was linearized with Not1 and transfected into 293 cells to produce the recombinant adenovirus vector Ad11-Tel-nsIL-12.

EXAMPLE 4

IL-12 Expression of Ad-TD-nsIL-12 and VV-TK-nsIL-12 in Tumor Cells

The cultured human pancreatic cancer Suit2 and Capan1, head and neck tumor EC9706, lung cancer A549 and H1299, esophageal cancer EC9706 and ZZB, ovarian cancer SKOV3, colorectal cancer SW620 and HCT116 as well as gastric cancer AGS cells were digested with trypsin, counted, loaded to 6-well plates, $2 \times 10^5$ cells/well, and separately infected with Ad-TD-nsIL-12 and VV-TK-nsIL-12, supernatants and cell mixtures were collected, respectively, and their IL-12 expression levels were detected by ELISA. The results are shown in FIG. 5 and FIG. 6.

Figure 5:
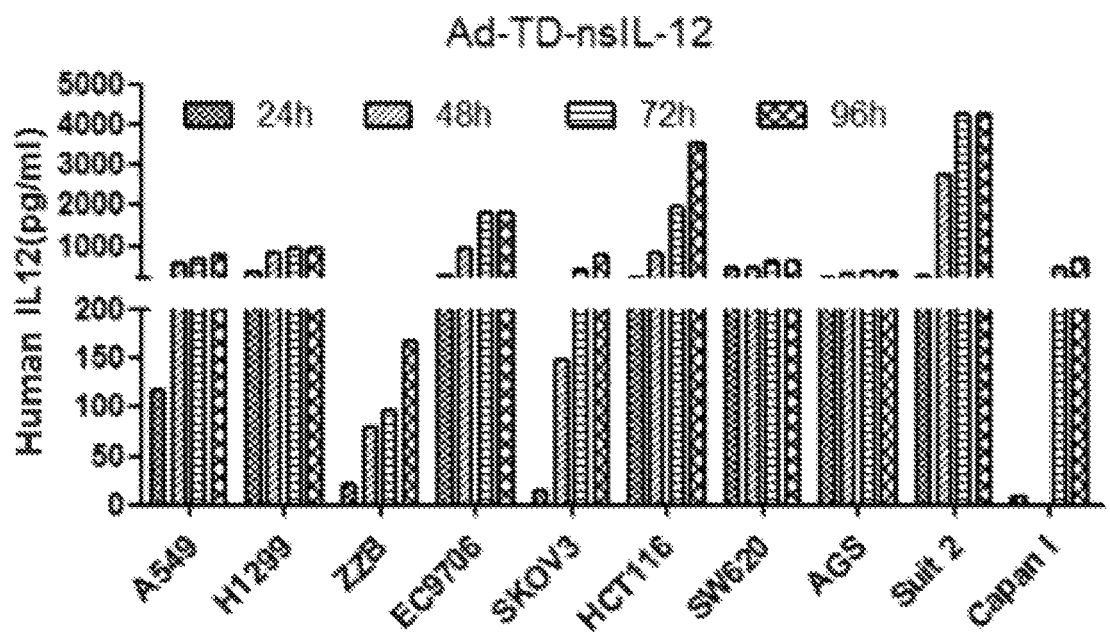
FIG. 5: IL-12 expression of Ad-TD-nsIL-12 in cells.
Figure 6:
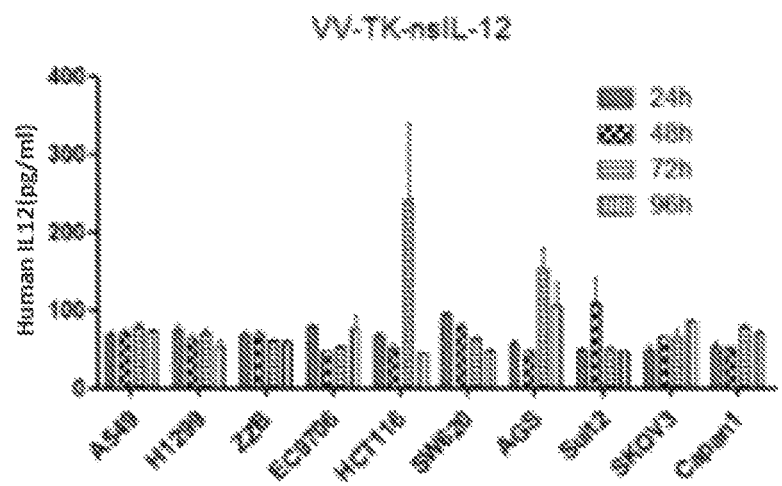
FIG. 6: IL-12 expression of VV-TK-nsIL-12 in cells.

FIG. 5 shows that Ad-TD-nsIL-12 expressed IL-12 in tumor cells, and FIG. 6 shows that VV-TK-nsIL-12 expressed IL-12 in tumor cells.

EXAMPLE 5

Anti-Tumor Effect of Ad-TD-nsIL-12 on Various Solid Tumors

The cultured pancreatic cancer SUIT2 and Capan1, head and neck cancer EC9706, lung cancer A549 and H1299, esophageal cancer EC9706 and ZZB, ovarian cancer SKOV3, colorectal cancer SW620 and HCT116 as well as gastric cancer AGS cells, were digested with trypsin, countered, turned into a cell suspension with DMEM containing 2% FBS, inoculated in the center of a 96-well plate, in which B1 to G1 were cell-free medium and the other three were PBS.

After 24-18 h, multiple proportion dilution of virus VV-TK/Ad-TD-nsIL-12, VV-TK/Ad-TD-IL-12 (full length human IL-12) and Ad-TD-LUC (LUC, Luciferase) or VV-TK-RFP was preformed, in which with $1 \times 10^4$ pfu/cell as initial concentration, 10 times dilution was applied to these virus solutions to form nine gradients of dilution, and the last row of cells was not added with virus. After the multiple proportion dilution, the virus was added to the center of 96-well plate by using a volley pipettor, with 10 μl/well and the same virus gradient in each row.

The virus-infected cells were returned to a 37° C. incubator. After 6 days, 20 μl of a mixture solution of MTS and PMS, 20:1 (MTS:PMS), was added to each well other than those added with PBS. After 1-4 h, the solution was taken out and measured with microplate reader to determine absorbance at wavelength of 490 nm. EC50 was calculated accordingly and the results were shown in FIGS. 7 and 8.

Figure 7:
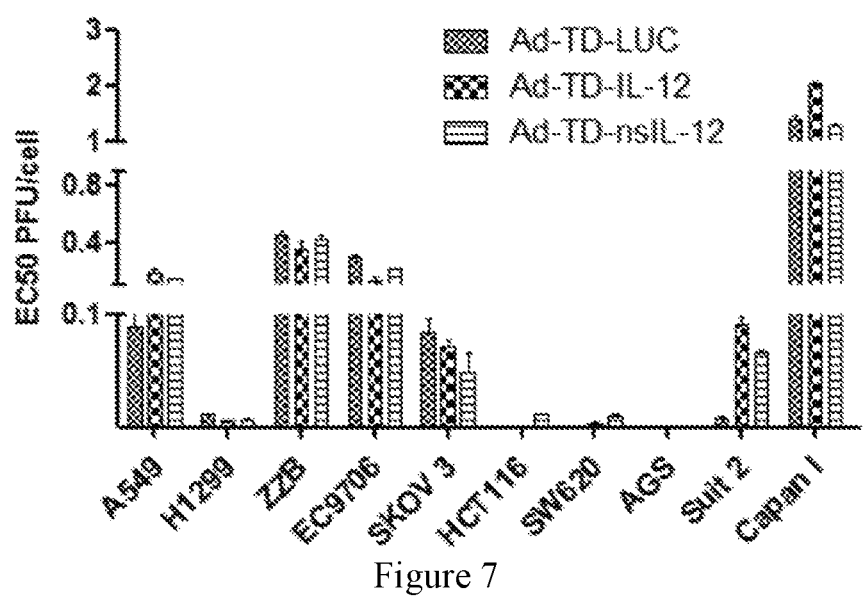
FIG. 7: Anti-tumor effect of Ad-TD-nsIL-12 on different types of solid tumors.
Figure 8:
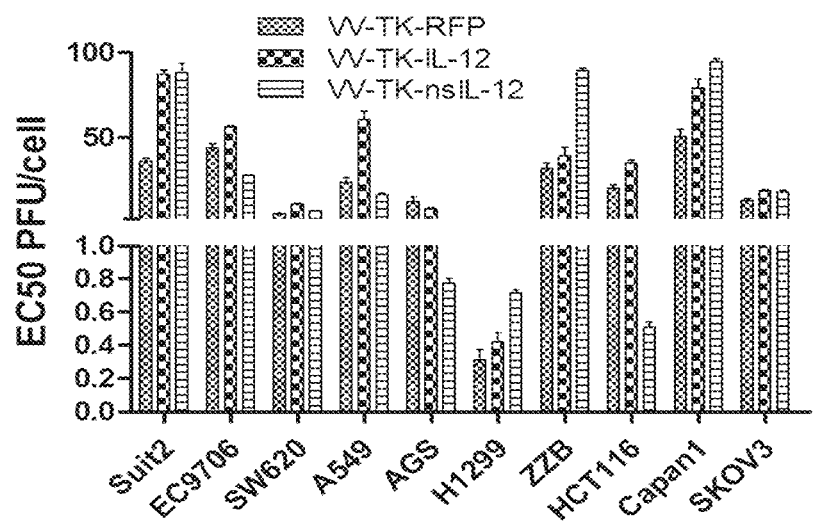
FIG. 8: Anti-tumor effect of VV-TK-nsIL-12 on different types of solid tumors.

FIGS. 7 and 8 show that Ad-TD-nsIL-12 and VV-TK-nsIL-12 had the ability to kill various solid tumor cells.

EXAMPLE 6

Comparison of Changes in IL-12 Expression of Ad-TD-nsIL-12 Versus Ad-TD-LUC and Ad-TD-IL-12 After Intraperitoneal Injection Once in Tumor-Bearing Syrian Hamsters $1 \times 10^7$ SHPC6 cells (Syrian hamster pancreatic cancer cells, supplied by WSM Wold of St. Louis University) were intraperitoneally inoculated into 5 to 6 weeks old Syrian hamsters, and the animals were divided into 4 groups after 4 days, 9 animals per group. The animals were separately intraperitoneally injected once with 500 μl of PBS, 1×10$^9$ PFU Ad-TD-LUC (LUC was derived from pGL3 vector luciferase, constructed according to the method for construction of Ad-TD-nsIL-12 in Example 1), Ad-TD-IL-12 (full length human IL-12, constructed according to the method for construction of Ad-TD-nsIL-12 as described in Example 1), or Ad-TD-nsIL-12. On the 1$^{st}$, 3$^{rd}$ and 5$^{th}$ day after injection, serum samples were collected and analyzed to determine changes of IL-12 expression in peripheral blood, and the results were shown in FIG. 9.

Figure 9:
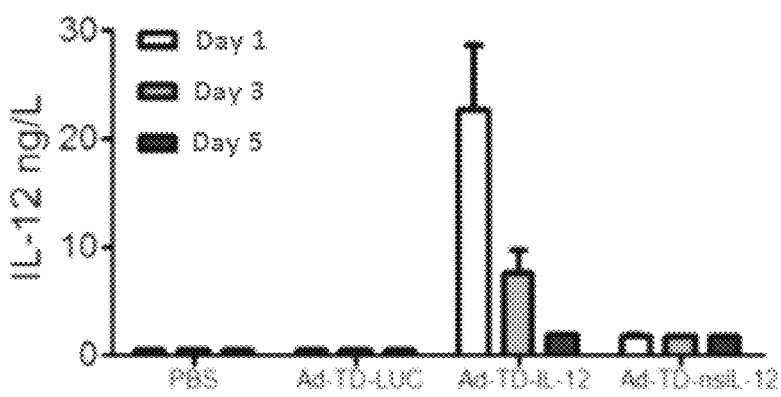
FIG. 9: Expression of IL-12 in peripheral blood of tumor-bearing Syrian hamsters injected with different viral vectors.

The results of FIG. 9 show that the expression of IL-12 was high in the Ad-TD-IL-12 group animals on the 1$^{st}$ day after the injection of virus vector, and the expression of IL-12 on the 3$^{rd}$ and 5$^{th}$ day was significantly decreased, showing a significant change in IL-12 expression level; while the Ad-TD-nsIL-12 group animals showed a constant expression of IL-12 at a low level for each day, that was, the expression of IL-12 showed no significant difference from the 1$^{st}$ day to the 5$^{th}$ day, suggesting that Ad-TD-nsIL-12 was unlikely to produce IL-12 in a large amount that would cause toxic and side effects in vivo.

EXAMPLE 7

Antitumor Application of Tumor Targeting Adenovirus Ad-TD-nsIL-12 and Comparison Thereof with Ad-TD-LUC and Ad-TD-IL-12

1×10$^6$ HPD1-NR (Syrian hamster pancreatic cancer cells, donated by WSM Wold, University of St. Louis, USA) were inoculated on the right upper side of back of each of 5 to 6 weeks old Syrian hamsters. The average tumor volume of each group of animals was about 330 mm$^3$. Intratumoral injection was carried out with PBS, Ad-TD-LUC, Ad-TD-IL-12 and Ad-TD-nsIL-12, respectively. The viral vector was injected at a dose of 1×10$^9$ PFU, once per day, for total 6 times, and tumor growth curves and tumor free rates were observed. The results were shown in FIG. 10 and FIG. 11.

Figure 10:
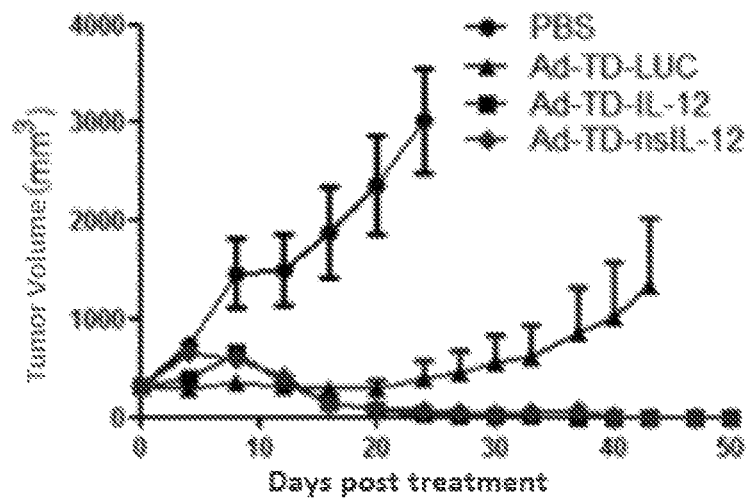
FIG. 10: Comparison of anti-tumor effects of Ad-TD-nsIL-12 with Ad-TD-LUC and Ad-TD-IL-12 in Syrian hamster subcutaneous transplanted tumor models of pancreatic cancer.
Figure 11:
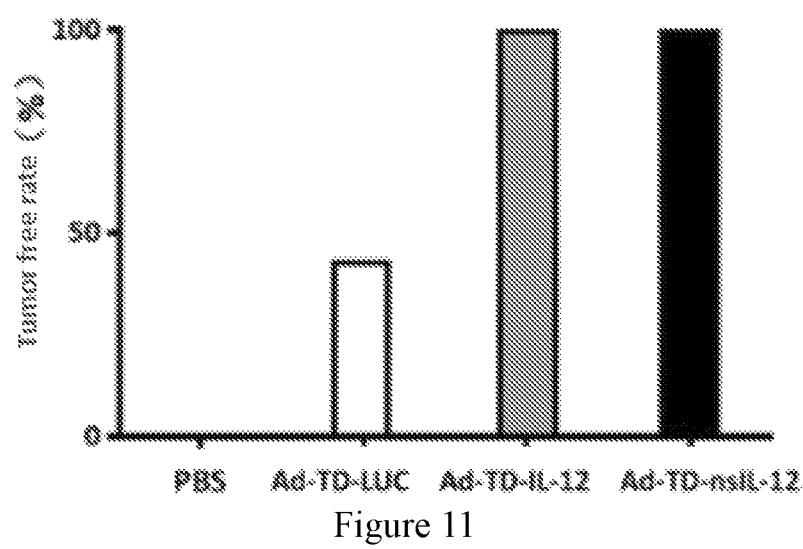
FIG. 11: Comparison of tumor free rates of Ad-TD-nsIL-12 with Ad-TD-LUC and Ad-TD-IL-12 in Syrian hamster subcutaneous transplanted tumor models of pancreatic cancer.

FIG. 10 shows that Ad-TD-nsIL-12 and Ad-TD-IL-12 showed stronger antitumor effects than the control vector Ad-TD-LUC and PBS; FIG. 11 shows that Ad-TD-nsIL-12 and Ad-TD-IL-12 treatment groups had a very high tumor free rate of up to 100%, while the Ad-TD-LUC group had a tumor free rate of only 42.8%.

EXAMPLE 8

Therapeutic Effect of Ad-TD-nsIL-12 on In Situ Model of Pancreatic Carcinoma in Syrian Hamsters and Comparison Thereof with Ad-TD-LUC and Ad-TD-IL-12

Anesthetization of 4 to 5 weeks old Syrian hamsters was carried out by using 10% chloral hydrate, the left abdomen of Syrian hamster was opened, pancreas that linked with spleen was found, 3×10$^6$ HapT1 cells (Syrian hamster pancreatic cancer cells, provided by WSM Wold, University of St. Louis) were inoculated to pancreas parenchyma. Six days later, the tumor-bearing animals were divided into 4 groups, 7 animals per group. Intraperitoneal injection of 500 μl of PBS, 1×10$^9$ PFU of Ad-TD-LUC, Ad-TD-IL-12 or Ad-TD-nsIL-12 was performed respectively for treatment, once per every other day, for total 6 times. Survival time of animal was observed, and the results were shown in FIG. 12.

Figure 12:
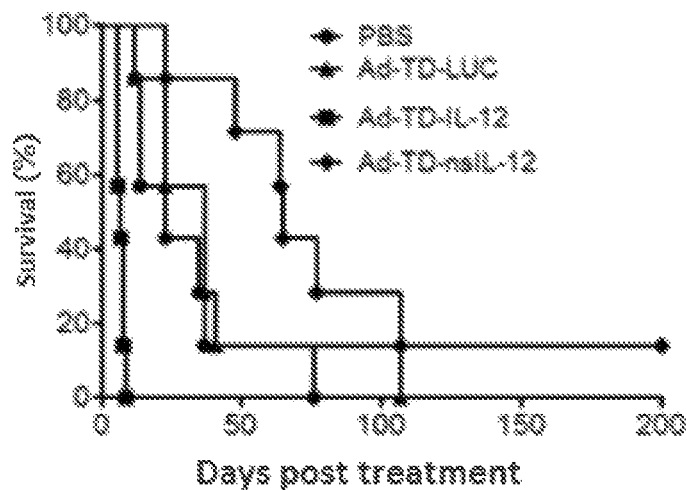
FIG. 12: Comparison of anti-tumor effects of Ad-TD-nsIL-12 with Ad-TD-LUC and Ad-TD-IL-12 in Syrian hamster orthotopic models of pancreatic cancer.

The results of FIG. 12 show that Ad-TD-nsIL-12 had better therapeutic effect than Ad-TD-LUC and Ad-TD-IL-12, and was capable of significantly prolonging the survival time of the tumor-bearing animals. The death of all animals of Ad-TD-IL-12 group was significantly earlier than that of PBS group and other groups, suggesting that full length IL-12 could cause animal death due to its toxicity.

EXAMPLE 9

Therapeutic Effects of Ad-TD-LUC, Ad-TD-IL-12 and Ad-TD-nsIL-12 on Peritoneally Disseminated PaCa in Syrian Hamsters 1×10$^7$ SHPC6 cells were inoculated into the abdominal cavity of each of 4 to 5 weeks old Syrian hamsters. Four days later, the animals were divided into 4 groups, 10 animals per group. Intraperitoneal injection of 500 μl of PBS, 1×10$^9$ PFU of Ad-TD-LUC, Ad-TD-IL-12 or Ad-TD-nsIL-12 was performed separately for treatment, once per every other day, for total 3 times. Survival time of the animals was observed, and the results were shown in FIG. 13.

Figure 13:
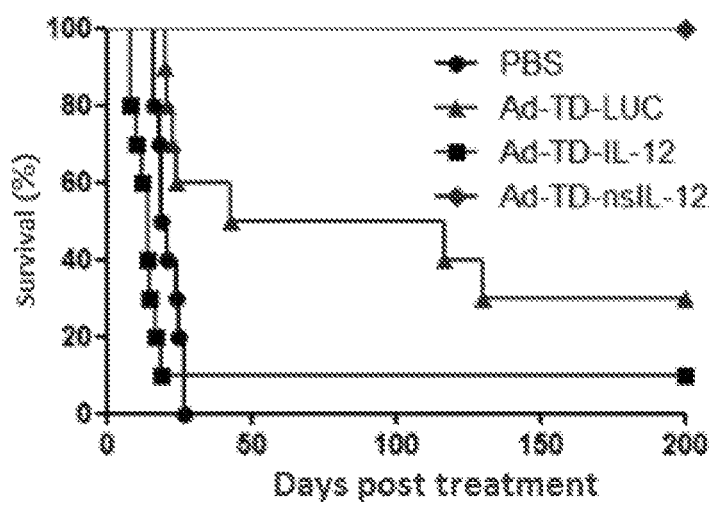
FIG. 13: Comparison of anti-tumor effects of Ad-TD-nsIL-12 with Ad-TD-LUC and Ad-TD-IL-12 in Syrian hamster intraperitoneally disseminated tumor models of pancreatic cancer.

The results of FIG. 13 show that the animals in the Ad-TD-nsIL-12 treatment group had survival rate of 100% during the observation period (200 days after the first treatment), whereas the animals in the Ad-TD-LUC group and the Ad-TD-IL-12 group had survival rates of 30% and 10%, respectively, and the death of the Ad-TD-IL-12 group animals was earlier than that of PBS group and other groups, suggesting that the full length IL-12 could lead to animal death due to its toxicity.

EXAMPLE 10

Comparison of Hepatotoxicity Between Ad-TD-nsIL-12 and Ad-TD-IL-12 After Intraperitoneal Injection in Syrian Hamsters 1×10$^7$ SHPC6 cells were inoculated into the abdominal cavity of 5-6 weeks old Syrian hamsters, the animals were grouped after 4 days, 9 animals per group. Intraperitoneal injection of 500 μl PBS, 1×10$^9$ of PFU Ad-TD-LUC, Ad-TD-nsIL-12 or 5×10$^8$ of Ad-TD-IL-12 was performed once, and serum samples were collected on the 1$^{st}$, 3$^{rd}$ and 5$^{th}$ day after the injection. Alanine aminotransferase (ALT), aspartate aminotransferase (AST) and alkaline phosphatase (ALP) were detected, and the results were shown in FIG. 14.

Figure 14:
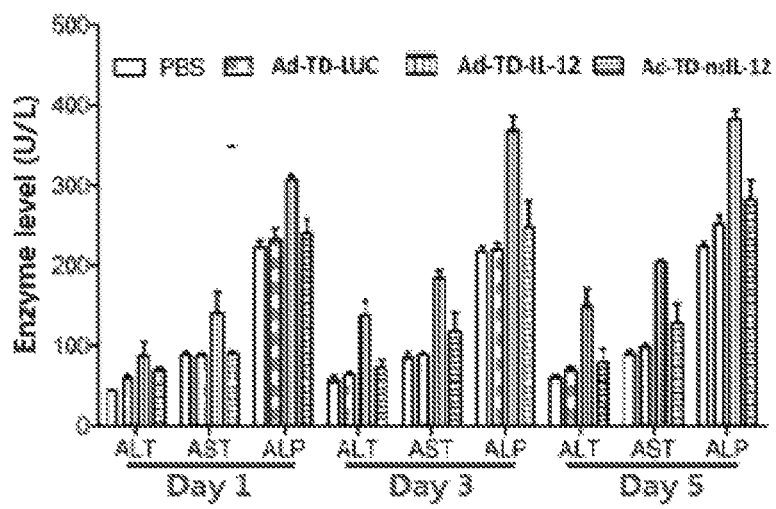
FIG. 14: Comparison of hepatotoxicity of Ad-TD-nsIL-12 with Ad-TD-LUC and Ad-TD-IL-12 in Syrian hamster intraperitoneally disseminated tumor models of pancreatic cancer.

The results of FIG. 14 show that the increases of ALT, AST and ALP induced by Ad-TD-nsIL-12 were significantly lower than those of Ad-TD-IL-12, indicating that Ad-TD-nsIL-12 had a hepatotoxicity significantly lower than that of Ad-TD-IL-12.

EXAMPLE 11

Comparison of Anti-Tumor Effect of Ad-TD-nsIL-12 on Subcutaneous Hamster Tumor Model of Head and Neck Tumor 1×10$^7$ HCPC1 cells (Syrian hamster head and neck tumor cells) were inoculated on the right upper part of back of each of 5 to 6 weeks old Syrian hamsters. When the average tumor volume of each group was about 330 mm$^3$, PBS, Ad-TD-LUC and Ad-TD-nsIL-12 were injected in tumors, respectively. The viral vector was injected with 5×10$^7$ PFU each time, once per day, for total 6 times. The tumor growth curves and tumor free rates were observed, and the results were shown in FIG. 15.

Figure 15:
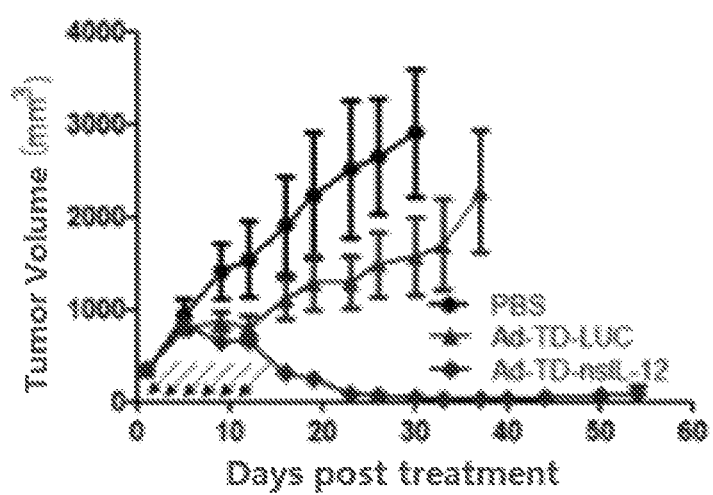
FIG. 15: Comparison of anti-tumor effects of Ad-TD-nsIL-12 in Syrian hamster subcutaneous transplanted tumor models of head and neck tumor.

The results of FIG. 15 show that Ad-TD-nsIL-12 showed a stronger antitumor effect than the control viral vector Ad-TD-LUC and PBS.

EXAMPLE 12

Comparison of Anti-Tumor Effect of VV-TK-nsIL-12 Versus VV-TK-RFP and VV-TK-IL-12 on Peritoneally Disseminated PaCa in Syrian Hamsters $1\times10^7$ SHPC6 cells were inoculated into abdominal cavity of each of 4 to 5 weeks old Syrian hamsters. Four days later, the animals were divided into four groups, 10 animals per group. Intraperitoneal injection of 500 μl PBS, $4\times10^7$ PFU VV-TK-RFP (inserted with red fluorescent protein, constructed according to the method for construction of VV-TK-nsIL-12), VV-TK-IL-12 (inserted with full length human IL-12 gene, constructed according to the method for construction of VV-TK-nsIL-12) or VV-TK-nsIL-12 was performed for treatment, once per every other day, for total 3 times. The survival time of animals was observed, and the results were shown in FIG. 16.

Figure 16:
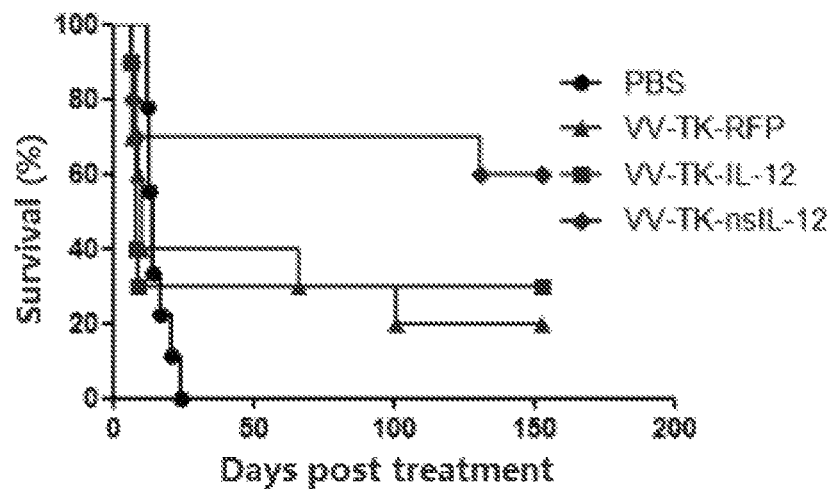
FIG. 16: Comparison of anti-tumor effects of VV-TK-nsIL-12 versus VV-TK-RFP and VV-TK-IL-12 in Syrian hamster intraperitoneally disseminated tumor models of pancreatic cancer.

The results of FIG. 16 show that VV-TK-nsIL-12 had better therapeutic effect than VV-TK-RFP and VV-TK-IL-12, and was capable of significantly prolonging the survival time of tumor-bearing animals.

EXAMPLE 13

Comparison of Anti-Tumor Effect of Ad11-Tel-nsIL-12 Versus Ad11-Tel-GFP and Ad11-Tel-IL-12 on Peritoneally Disseminated PaCa in Syrian Hamsters $1\times10^7$ SHPC6 cells were inoculated into the abdominal cavity of each of 4 to 5 weeks old Syrian hamsters. Four days later, the animals were divided into 4 groups, 10 animals per group. Intraperitoneal injection of 500 μl of PBS, $1\times10^9$ PFU of Ad11-Tel-GFP (inserted with green fluorescent protein, constructed according to the method for construction of Ad11-Tel-nsIL-12), Ad11-Tel-IL-12 (inserted with full length human IL-12 gene, constructed according to the method for construction of Ad11-Tel-nsIL-12) or Ad11-Tel-nsIL-12 was performed for treatment, once per every other day, for total 3 times. The survival time of animals was observed, and the results were shown in FIG. 17.

Figure 17:
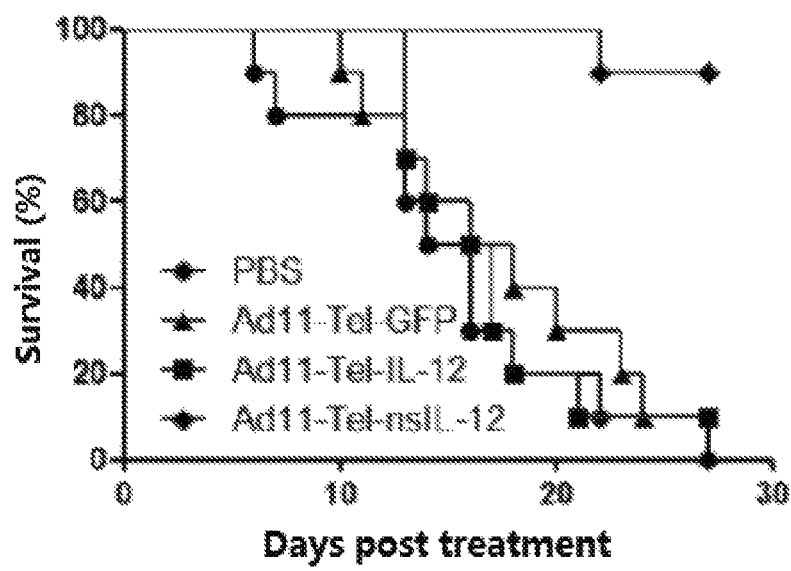
FIG. 17: Comparison of anti-tumor effects of Ad11-Tel-nsIL-12 versus Ad11-Tel-GFP and Ad11-Tel-IL-12 in Syrian hamster intraperitoneally disseminated tumor models of pancreatic cancer.

The results of FIG. 17 show that Ad11-Tel-nsIL-12 had better therapeutic effect than Ad11-Tel-GFP and Ad11-Tel-IL-12, and was able to significantly prolong the survival time of tumor-bearing animals.

Finally, it should be noted that the above embodiments are merely illustrative of the technical aspects of the present invention and are not restrictive. Although the present invention has been described in detail with reference to preferred embodiments, it will be understood by those skilled in the art that the technical solutions of the present invention can be modified or equivalently replaced without departing from the spirit and scope of the technical solution of the invention, and all of these changes are intended to be included within the scope of the claims of the invention.

What is claimed is:

1. A recombinant vector, which is an oncolytic virus and comprises a nucleotide sequence encoding a modified IL-12, which is non-secretory, wherein the non-secretory IL-12 has the following structure: p40-linker-p35 or p35-linker-p40; and wherein the non-secretory IL-12 does not contain a secretory signal peptide, and wherein the recombinant vector is the viral vector with the CCTCC Accession NO: V201520.

2. A method for treatment of a disease associated with IL-12, which comprises administering to a subject the recombinant vector according to claim 1.

3. The method according to claim 2, wherein the disease is a cancer.

4. The method according to claim 2, wherein the disease is pancreatic cancer, head and neck cancer, lung cancer, esophageal cancer, ovarian cancer, colorectal cancer, colon cancer or gastric cancer.

5. The method according to claim 2, wherein the disease is an intraperitoneally disseminated tumor.

* * * * *

UNITED STATES PATENT AND TRADEMARK OFFICE
CERTIFICATE OF CORRECTION

PATENT NO. : 11,345,732 B2  
APPLICATION NO. : 15/758853  
DATED : May 31, 2022  
INVENTOR(S) : Yaohe Wang et al.

Page 1 of 1

It is certified that error appears in the above-identified patent and that said Letters Patent is hereby corrected as shown below:

On the Title Page

Item (73) should read:  
(73) Assignees: BEIJING BIO-TARGETING THERAPEUTICS TECHNOLOGY INC., Beijing (CN)

Signed and Sealed this  
Sixth Day of May, 2025

Coke Morgan Stewart  
*Acting Director of the United States Patent and Trademark Office*

SEQUENCE LISTING

<160> NUMBER OF SEQ ID NOS: 12

<210> SEQ ID NO 1
<211> LENGTH: 1548
<212> TYPE: DNA
<213> ORGANISM: Artificial sequence
<220> FEATURE:
<223> OTHER INFORMATION: nsIL-12

<400> SEQUENCE: 1

```
atgatatggg aactgaagaa agatgtttat gtcgtagaat tggattggta tccggatgcc      60
cctggagaaa tggtggtcct cacctgtgac accoctgaag aagatggtat cacctggacc     120
ttggaccaga gcagtgaggt cttaggctct ggcaaaaccc tgaccatcca agtcaaagag     180
tttggagatg ctggccagta cacctgtcac aaaggaggcg aggttctaag ccattcgctc     240
ctgctgcttc acaaaaagga agatggaatt tggtccactg atatttaaa ggaccagaaa      300 gaacccaaaa ataagacctt tctaagatgc gaggccaaga attattctgg acgtttcacc     360
tgctggtggc tgacgacaat cagtactgat ttgacattca gtgtcaaaag cagcagaggc     420
tcttctgacc cccaagggt gacgtgcgga gctgctacac tctctgcaga gagagtcaga     480
ggggacaaca aggagtatga gtactcagtg gagtgccagg aggacagtgc ctgcccagct     540
gctgaggaga gtctgcccat tgaggtcatg gtggatgccg ttcacaagct caagtatgaa      600
aactacacca gcagcttctt catcagggac atcatcaaac ctgacccacc caagaacttg     660
cagctgaagc cattaaagaa ttctcggcag gtggaggtca gctgggagta ccctgacacc     720
tggagtactc cacattccta cttctccctg acattctgcg ttcaggtcca gggcaagagc     780
```

```
aagagagaaa agaaagatag agtcttcacg acaagacct cagccacggt catctgccgc     840
aaaaatgcca gcattagcgt gcgggcccag accgctact atagctcatc ttggagcgaa     900
tgggcatctg tgccctgcag tgttcctgga gtagggggttc ctggagtagg ggccagaaac   960
ctccccgtgg ccactccaga cccaggaatg ttcccatgcc ttcaccactc ccaaaacctg    1020
ctgagggccg tcagcaacat gctccagaag gccagacaaa ctctagaatt ttacccttgc    1080
acttctgaag agattgatca tgaagatatc acaaaagata aaaccagcac agtggaggcc    1140
tgtttaccat tggaattaac caagaatgag agttgcctaa attccagaga gacctctttc    1200
ataactaatg ggagttgcct ggcctccaga aagacctctt ttatgatggc cctgtgcctt    1260
agtagtattt atgaagactt gaagatgtac caggtggagt tcaagaccat gaatgcaaag    1320
ctgctgatgg atcctaagag gcagatcttt ctagatcaaa acatgctggc agttattgat    1380
gagctgatgc aggccctgaa tttcaacagt gagactgtgc cacaaaaatc ctcccttgaa    1440
gaaccggatt tttataaaac taaaatcaag ctctgcatac ttcttcatgc tttcagaatt    1500
cgggcagtga ctattgatag agtgatgagc tatctgaatg cttcctaa                1548
```

<210> SEQ ID NO 2
<211> LENGTH: 515
<212> TYPE: PRT
<213> ORGANISM: Artificial sequence
<220> FEATURE:
<223> OTHER INFORMATION: nsIL-12

<400> SEQUENCE: 2

```
Met Ile Trp Glu Leu Lys Lys Asp Val Tyr Val Val Glu Leu Asp Trp
1               5                   10                  15

Tyr Pro Asp Ala Pro Gly Glu Met Val Val Leu Thr Cys Asp Thr Pro
            20                  25                  30

Glu Glu Asp Gly Ile Thr Trp Thr Leu Asp Gln Ser Ser Glu Val Leu
        35                  40                  45

Gly Ser Gly Lys Thr Leu Thr Ile Gln Val Lys Glu Phe Gly Asp Ala
    50                  55                  60

Gly Gln Tyr Thr Cys His Lys Gly Gly Glu Val Leu Ser His Ser Leu
65                  70                  75                  80

Leu Leu Leu His Lys Lys Glu Asp Gly Ile Trp Ser Thr Asp Ile Leu
                85                  90                  95

Lys Asp Gln Lys Glu Pro Lys Asn Lys Thr Phe Leu Arg Cys Glu Ala
            100                 105                 110

Lys Asn Tyr Ser Gly Arg Phe Thr Cys Trp Trp Leu Thr Thr Ile Ser
        115                 120                 125

Thr Asp Leu Thr Phe Ser Val Lys Ser Ser Arg Gly Ser Ser Asp Pro
    130                 135                 140

Gln Gly Val Thr Cys Gly Ala Ala Thr Leu Ser Ala Glu Arg Val Arg
145                 150                 155                 160

Gly Asp Asn Lys Glu Tyr Glu Tyr Ser Val Glu Cys Gln Glu Asp Ser
                165                 170                 175

Ala Cys Pro Ala Ala Glu Glu Ser Leu Pro Ile Glu Val Met Val Asp
            180                 185                 190

Ala Val His Lys Leu Lys Tyr Glu Asn Tyr Thr Ser Ser Phe Phe Ile
        195                 200                 205

Arg Asp Ile Ile Lys Pro Asp Pro Pro Lys Asn Leu Gln Leu Lys Pro
    210                 215                 220
```

Leu Lys Asn Ser Arg Gln Val Glu Val Ser Trp Glu Tyr Pro Asp Thr
225                 230                 235                 240

Trp Ser Thr Pro His Ser Tyr Phe Ser Leu Thr Phe Cys Val Gln Val
            245                 250                 255

Gln Gly Lys Ser Lys Arg Glu Lys Lys Asp Arg Val Phe Thr Asp Lys
        260                 265                 270

Thr Ser Ala Thr Val Ile Cys Arg Lys Asn Ala Ser Ile Ser Val Arg
    275                 280                 285

Ala Gln Asp Arg Tyr Tyr Ser Ser Ser Trp Ser Glu Trp Ala Ser Val
290                 295                 300

Pro Cys Ser Val Pro Gly Val Gly Val Pro Gly Val Gly Ala Arg Asn
305                 310                 315                 320

Leu Pro Val Ala Thr Pro Asp Pro Gly Met Phe Pro Cys Leu His His
            325                 330                 335

Ser Gln Asn Leu Leu Arg Ala Val Ser Asn Met Leu Gln Lys Ala Arg
        340                 345                 350

Gln Thr Leu Glu Phe Tyr Pro Cys Thr Ser Glu Glu Ile Asp His Glu
    355                 360                 365

Asp Ile Thr Lys Asp Lys Thr Ser Thr Val Glu Ala Cys Leu Pro Leu
370                 375                 380

Glu Leu Thr Lys Asn Glu Ser Cys Leu Asn Ser Arg Glu Thr Ser Phe
385                 390                 395                 400

Ile Thr Asn Gly Ser Cys Leu Ala Ser Arg Lys Thr Ser Phe Met Met
            405                 410                 415

Ala Leu Cys Leu Ser Ser Ile Tyr Glu Asp Leu Lys Met Tyr Gln Val
        420                 425                 430

Glu Phe Lys Thr Met Asn Ala Lys Leu Leu Met Asp Pro Lys Arg Gln
    435                 440                 445

Ile Phe Leu Asp Gln Asn Met Leu Ala Val Ile Asp Glu Leu Met Gln
450                 455                 460

Ala Leu Asn Phe Asn Ser Glu Thr Val Pro Gln Lys Ser Ser Leu Glu
465                 470                 475                 480

Glu Pro Asp Phe Tyr Lys Thr Lys Ile Lys Leu Cys Ile Leu Leu His
            485                 490                 495

Ala Phe Arg Ile Arg Ala Val Thr Ile Asp Arg Val Met Ser Tyr Leu
        500                 505                 510

Asn Ala Ser
    515

<210> SEQ ID NO 3
<211> LENGTH: 597
<212> TYPE: DNA
<213> ORGANISM: Artificial sequence
<220> FEATURE:
<223> OTHER INFORMATION: ns-p35

<400> SEQUENCE: 3
gccagaaacc tccccgtggc cactccagac ccaggaatgt tcccatgcct tcaccactcc      60
caaaacctgc tgagggccgt cagcaacatg ctccagaagg ccagacaaac tctagaattt     120 taccccttgca cttctgaaga gattgatcat gaagatatca aaagataa aaccagcaca     180 gtggaggcct gtttaccatt ggaattaacc aagaatgaga gttgcctaaa ttccagagag     240
acctctttca taactaatgg agttgcctg gcctccagaa agacctcttt tatgatggcc     300
ctgtgcctta gtagtattta tgaagacttg aagatgtacc aggtggagtt caagaccatg     360

-continued

```
aatgcaaagc tgctgatgga tcctaagagg cagatctttc tagatcaaaa catgctggca    420
gttattgatg agctgatgca ggccctgaat tcaacagtg agactgtgcc acaaaaatcc     480
tcccttgaag aaccggattt ttataaaact aaaatcaagc tctgcatact tcttcatgct    540
ttcagaattc gggcagtgac tattgataga gtgatgagct atctgaatgc ttcctaa      597
```

```
<210> SEQ ID NO 4
<211> LENGTH: 921
<212> TYPE: DNA
<213> ORGANISM: Artificial sequence
<220> FEATURE:
<223> OTHER INFORMATION: ns-p40

<400> SEQUENCE: 4
```

```
atgatatggg aactgaagaa agatgtttat gtcgtagaat tggattggta tccggatgcc     60
cctggagaaa tggtggtcct cacctgtgac acccctgaag aagatggtat cacctggacc    120
ttggaccaga gcagtgaggt cttaggctct ggcaaaaccc tgaccatcca agtcaaagag    180
tttggagatg ctggccagta cacctgtcac aaaggaggcg aggttctaag ccattcgctc    240
ctgctgcttc acaaaaagga agatggaatt tggtccactg atattttaaa ggaccagaaa    300
gaacccaaaa ataagacctt tctaagatgc gaggccaaga attattctgg acgtttcacc    360
tgctggtggc tgacgacaat cagtactgat ttgacattca gtgtcaaaag cagcagaggc    420
tcttctgacc cccaagggt gacgtgcgga gctgctacac tctctgcaga gagagtcaga    480
ggggacaaca aggagtatga gtactcagtg gagtgccagg aggacagtgc ctgcccagct    540
gctgaggaga gtctgcccat tgaggtcatg gtggatgccg ttcacaagct caagtatgaa    600
aactacacca gcagcttctt catcagggac atcatcaaac ctgacccacc caagaacttg    660
cagctgaagc cattaaagaa ttctcggcag gtggaggtca gctgggagta ccctgacacc    720
tggagtactc cacattccta cttctccctg acattctgcg ttcaggtcca gggcaagagc    780
aagagagaaa agaaagatag agtcttcacg gacaagacct cagccacggt catctgccgc    840
aaaaatgcca gcattagcgt gcgggcccag gaccgctact atagctcatc ttggagcgaa    900
tgggcatctg tgccctgcag t                                              921
```

```
<210> SEQ ID NO 5
<211> LENGTH: 198
<212> TYPE: PRT
<213> ORGANISM: Artificial sequence
<220> FEATURE:
<223> OTHER INFORMATION: ns-p35

<400> SEQUENCE: 5
```

```
Ala Arg Asn Leu Pro Val Ala Thr Pro Asp Pro Gly Met Phe Pro Cys
1               5                   10                  15

Leu His His Ser Gln Asn Leu Leu Arg Ala Val Ser Asn Met Leu Gln
            20                  25                  30

Lys Ala Arg Gln Thr Leu Glu Phe Tyr Pro Cys Thr Ser Glu Glu Ile
        35                  40                  45

Asp His Glu Asp Ile Thr Lys Asp Lys Thr Ser Thr Val Glu Ala Cys
    50                  55                  60

Leu Pro Leu Glu Leu Thr Lys Asn Glu Ser Cys Leu Asn Ser Arg Glu
65                  70                  75                  80

Thr Ser Phe Ile Thr Asn Gly Ser Cys Leu Ala Ser Arg Lys Thr Ser
                85                  90                  95

Phe Met Met Ala Leu Cys Leu Ser Ser Ile Tyr Glu Asp Leu Lys Met
```

```
            100                 105                 110
Tyr Gln Val Glu Phe Lys Thr Met Asn Ala Lys Leu Leu Met Asp Pro
            115                 120                 125

Lys Arg Gln Ile Phe Leu Asp Gln Asn Met Leu Ala Val Ile Asp Glu
            130                 135                 140

Leu Met Gln Ala Leu Asn Phe Asn Ser Glu Thr Val Pro Gln Lys Ser
145                 150                 155                 160

Ser Leu Glu Glu Pro Asp Phe Tyr Lys Thr Lys Ile Lys Leu Cys Ile
            165                 170                 175

Leu Leu His Ala Phe Arg Ile Arg Ala Val Thr Ile Asp Arg Val Met
            180                 185                 190

Ser Tyr Leu Asn Ala Ser
            195

<210> SEQ ID NO 6
<211> LENGTH: 307
<212> TYPE: PRT
<213> ORGANISM: Artificial sequence
<220> FEATURE:
<223> OTHER INFORMATION: ns-p40

<400> SEQUENCE: 6

Met Ile Trp Glu Leu Lys Lys Asp Val Tyr Val Val Glu Leu Asp Trp
1               5                   10                  15

Tyr Pro Asp Ala Pro Gly Glu Met Val Val Leu Thr Cys Asp Thr Pro
            20                  25                  30

Glu Glu Asp Gly Ile Thr Trp Thr Leu Asp Gln Ser Ser Glu Val Leu
            35                  40                  45

Gly Ser Gly Lys Thr Leu Thr Ile Gln Val Lys Glu Phe Gly Asp Ala
        50                  55                  60

Gly Gln Tyr Thr Cys His Lys Gly Gly Glu Val Leu Ser His Ser Leu
65                  70                  75                  80

Leu Leu Leu His Lys Lys Glu Asp Gly Ile Trp Ser Thr Asp Ile Leu
                85                  90                  95

Lys Asp Gln Lys Glu Pro Lys Asn Lys Thr Phe Leu Arg Cys Glu Ala
            100                 105                 110

Lys Asn Tyr Ser Gly Arg Phe Thr Cys Trp Trp Leu Thr Thr Ile Ser
            115                 120                 125

Thr Asp Leu Thr Phe Ser Val Lys Ser Ser Arg Gly Ser Ser Asp Pro
            130                 135                 140

Gln Gly Val Thr Cys Gly Ala Ala Thr Leu Ser Ala Glu Arg Val Arg
145                 150                 155                 160

Gly Asp Asn Lys Glu Tyr Glu Tyr Ser Val Glu Cys Gln Glu Asp Ser
            165                 170                 175

Ala Cys Pro Ala Ala Glu Glu Ser Leu Pro Ile Glu Val Met Val Asp
            180                 185                 190

Ala Val His Lys Leu Lys Tyr Glu Asn Tyr Thr Ser Ser Phe Phe Ile
            195                 200                 205

Arg Asp Ile Ile Lys Pro Asp Pro Pro Lys Asn Leu Gln Leu Lys Pro
            210                 215                 220

Leu Lys Asn Ser Arg Gln Val Glu Val Ser Trp Glu Tyr Pro Asp Thr
225                 230                 235                 240

Trp Ser Thr Pro His Ser Tyr Phe Ser Leu Thr Phe Cys Val Gln Val
            245                 250                 255

Gln Gly Lys Ser Lys Arg Glu Lys Lys Asp Arg Val Phe Thr Asp Lys
```

260                 265                 270
Thr Ser Ala Thr Val Ile Cys Arg Lys Asn Ala Ser Ile Ser Val Arg
            275                 280                 285

Ala Gln Asp Arg Tyr Tyr Ser Ser Trp Ser Glu Trp Ala Ser Val
        290                 295                 300

Pro Cys Ser
305

<210> SEQ ID NO 7
<211> LENGTH: 10
<212> TYPE: PRT
<213> ORGANISM: Artificial sequence
<220> FEATURE:
<223> OTHER INFORMATION: linker

<400> SEQUENCE: 7

Val Pro Gly Val Gly Val Pro Gly Val Gly
1               5                   10

<210> SEQ ID NO 8
<211> LENGTH: 30
<212> TYPE: DNA
<213> ORGANISM: Artificial sequence
<220> FEATURE:
<223> OTHER INFORMATION: Coding sequence of linker

<400> SEQUENCE: 8
gttcctggag tagggtacc tggggtgggc                                    30

<210> SEQ ID NO 9
<211> LENGTH: 48
<212> TYPE: DNA
<213> ORGANISM: Artificial sequence
<220> FEATURE:
<223> OTHER INFORMATION: Forward primers of ns-p35

<400> SEQUENCE: 9
gttcctggag tagggtacc tggggtgggc gccagaaacc tccccgtg                48

<210> SEQ ID NO 10
<211> LENGTH: 26
<212> TYPE: DNA
<213> ORGANISM: Artificial sequence
<220> FEATURE:
<223> OTHER INFORMATION: Reverse primer of ns-p35

<400> SEQUENCE: 10
gctacgtatt aggaagcatt cagata                                       26

<210> SEQ ID NO 11
<211> LENGTH: 30
<212> TYPE: DNA
<213> ORGANISM: Artificial sequence
<220> FEATURE:
<223> OTHER INFORMATION: Forward primers of ns-p40

<400> SEQUENCE: 11
cctacgtaat gatatgggaa ctgaagaaag                                   30

<210> SEQ ID NO 12
<211> LENGTH: 48
<212> TYPE: DNA
<213> ORGANISM: Artificial sequence
<220> FEATURE:
<223> OTHER INFORMATION: Reverse primer ns-p40

```
<400> SEQUENCE: 12
gcccacccca ggtaccccta ctccaggaac actgcagggc acagatgc                48
```